US010583071B2

(12) United States Patent
Jolliff et al.

(10) Patent No.: US 10,583,071 B2
(45) Date of Patent: Mar. 10, 2020

(54) PERSONAL CLEANSING COMPOSITIONS COMPRISING EXPANDED PERLITE MICROSPHERES

(71) Applicant: ImerTech SAS, Paris (FR)

(72) Inventors: Sam Jolliff, Cornwall (GB); Anabelle Huguette Renee Legrix, Cornwall (GB); Thierry Casteran, Balam (FR)

(73) Assignee: ImerTech SAS, Paris (FR)

( * ) Notice: Subject to any disclaimer, the term of this patent is extended or adjusted under 35 U.S.C. 154(b) by 0 days.

(21) Appl. No.: 16/428,487

(22) Filed: May 31, 2019

(65) Prior Publication Data

US 2019/0282456 A1 Sep. 19, 2019

Related U.S. Application Data

(63) Continuation of application No. 15/107,396, filed as application No. PCT/EP2014/079184 on Dec. 23, 2014, now Pat. No. 10,342,746.

(30) Foreign Application Priority Data

Dec. 23, 2013 (EP) .................................... 13290329
Dec. 23, 2013 (EP) .................................... 13290330
May 2, 2014 (EP) .................................... 14290134

(51) Int. Cl.

| C11D 3/14 | (2006.01) |
| A61K 8/02 | (2006.01) |
| C11D 11/00 | (2006.01) |
| C11D 17/00 | (2006.01) |
| A61K 8/25 | (2006.01) |
| A61K 8/04 | (2006.01) |
| A61K 8/46 | (2006.01) |
| A61Q 19/10 | (2006.01) |
| A61Q 5/02 | (2006.01) |
| A61K 8/26 | (2006.01) |
| C11D 3/12 | (2006.01) |
| A61K 8/19 | (2006.01) |
| A61Q 5/00 | (2006.01) |

(52) U.S. Cl.
CPC ............ *A61K 8/025* (2013.01); *A61K 8/0241* (2013.01); *A61K 8/042* (2013.01); *A61K 8/19* (2013.01); *A61K 8/25* (2013.01); *A61K 8/26* (2013.01); *A61K 8/463* (2013.01); *A61Q 5/02* (2013.01); *A61Q 19/10* (2013.01); *C11D 3/1293* (2013.01); *C11D 3/14* (2013.01); *C11D 11/0023* (2013.01); *C11D 17/003* (2013.01); *C11D 17/0013* (2013.01); *A61K 2800/28* (2013.01); *A61K 2800/412* (2013.01); *A61Q 5/006* (2013.01)

(58) Field of Classification Search
CPC ...... C11D 3/14; C11D 17/0013; C11D 17/003
See application file for complete search history.

(56) References Cited

U.S. PATENT DOCUMENTS

| 3,961,978 | A | * | 6/1976 | Brodmann | .......... C03B 19/1075 106/409 |
| 4,051,056 | A | * | 9/1977 | Hartman | .............. C11D 3/1293 510/369 |
| 4,051,156 | A | | 9/1977 | Guczoghy et al. | |
| 4,235,732 | A | | 11/1980 | Beyer | |
| 4,287,080 | A | | 9/1981 | Siklosi | |
| 4,786,432 | A | | 11/1988 | Kanfer et al. | |
| 5,076,955 | A | | 12/1991 | Ussat et al. | |
| 5,395,541 | A | | 3/1995 | Carpenter et al. | |
| 5,597,553 | A | | 1/1997 | Baffelli | |
| 6,015,782 | A | | 1/2000 | Petri et al. | |
| 8,518,380 | B2 | | 8/2013 | Balmelli et al. | |
| 2002/0039978 | A1 | | 4/2002 | Schultz et al. | |
| 2002/0082181 | A1 | * | 6/2002 | Humphrey | ......... C11D 3/38663 510/305 |
| 2005/0169868 | A1 | | 8/2005 | Mohammadi et al. | |
| 2006/0025319 | A1 | | 2/2006 | Subramanian et al. | |
| 2006/0075930 | A1 | | 4/2006 | Wang et al. | |

(Continued)

FOREIGN PATENT DOCUMENTS

| EP | 0353860 A2 | 2/1990 |
| EP | 0 490 103 A1 | 6/1992 |

(Continued)

OTHER PUBLICATIONS

Crown, Talc, PP, Composite grades, Matsushima Industries K.K. Product Introduction (3) [online], May 4, 2012, [retrieved on May 12, 2017], Retrieved from the Internet, URL, https://web.archive.org/web/20120504210723/http://www.matsumurasangyo.co.jp/crown-products/crown-talc_product3.html (cited as a reference which discloses a well-known technology) (3 pages).
Database GNPD [Online] Mintel, Jan. 1, 2010, "Natural Orange Pumice Hand Cleaner", XP002770617, Database accession No. 1247865 (3 pages).
Database GNPD [Online] Mintel, Dec. 1, 2012, "Chilling Effect Shampoo and Shower Gel", XP002770618, Database accession No. 1900002 (3 pages).

(Continued)

*Primary Examiner* — Charles I Boyer
(74) *Attorney, Agent, or Firm* — Finnegan, Henderson, Farabow, Garrett, & Dunner LLP

(57) ABSTRACT

A personal care composition comprising a cosmetically acceptable base and inorganic particulate material, for example, a shower gel or hair shampoo, and a method of making the personal care composition. A cleaning composition comprising a base and inorganic particulate material, for example, a hard surface cleansing composition, and a method of making the cleaning composition. A composition, for example, a personal care composition, use of an inorganic particulate material having a d50 of from about 0.1 μm to about 200 μm in such a composition, and a method for making such a composition.

16 Claims, 3 Drawing Sheets

(56) References Cited

U.S. PATENT DOCUMENTS

| | | | |
|---|---|---|---|
| 2007/0203240 A1* | 8/2007 | Oblong | A61K 8/40 |
| | | | 514/561 |
| 2009/0252691 A1 | 10/2009 | Gartstein | |
| 2009/0270298 A1 | 10/2009 | Compain | |
| 2011/0105375 A1 | 5/2011 | Myers et al. | |
| 2011/0120487 A1* | 5/2011 | Rollat-Corvol | A45D 19/02 |
| | | | 132/200 |
| 2012/0322713 A1* | 12/2012 | Perez-Prat Vinuesa | |
| | | | C11D 3/2072 |
| | | | 510/236 |
| 2013/0081556 A1* | 4/2013 | Wang | B01J 21/08 |
| | | | 106/420 |
| 2014/0141676 A1* | 5/2014 | Crandall | D04H 1/4291 |
| | | | 442/347 |

FOREIGN PATENT DOCUMENTS

| | | |
|---|---|---|
| EP | 1938786 A1 | 7/2008 |
| EP | 2 111 843 A2 | 10/2009 |
| GB | 1057316 | 2/1967 |
| JP | S 51-076685 A | 7/1976 |
| JP | S 54-148006 A | 11/1979 |
| JP | S 62-257993 A | 11/1987 |
| JP | 2000-504666 A | 4/2000 |
| JP | 2000-297297 A | 10/2000 |
| JP | 2001-031540 A | 2/2001 |
| JP | 2001-055320 A | 2/2001 |
| JP | 2002-097495 A | 4/2002 |
| JP | 2004-506581 A | 3/2004 |
| JP | 2006-341598 A | 12/2006 |
| JP | 2007-302625 A | 11/2007 |
| JP | 2008-044972 A | 2/2008 |
| JP | 2012-140363 A | 7/2012 |
| WO | WO 97/30126 | 8/1997 |
| WO | WO 00/74638 A1 | 12/2000 |
| WO | WO 01/30315 A1 | 5/2001 |
| WO | WO 2002/11882 | 2/2002 |
| WO | WO 2008 02197 | 1/2008 |
| WO | WO 2010/054921 A1 | 5/2010 |
| WO | WO 2011/100104 A1 | 8/2011 |
| WO | WO 2011/101239 A2 | 8/2011 |
| WO | WO 2013/053635 | 4/2013 |
| WO | WO 2014/037306 A1 | 3/2014 |

OTHER PUBLICATIONS

Database GNPD [Online] Mintel, Oct. 1, 2013, "Liquid Hand Cleaner", XP002770619, Database accession No. 2190163 (2 pages).
Dermagrain Microdermabrasion Crystals [online], Mar. 27, 2010, [retrieved on May 15, 2017], Retrieved from the Internet, URL, https://web.archive.org/web/20100327143259/http://www.dermagrain.com/techspecs.html (cited as a reference which discloses a well-known technology) (2 pages).
European Search Report dated Jun. 13, 2017, in European Application No. 17155616.0 (13 pages).
European Search Report dated Jun. 30, 2017, in European Application No. 17155618.6 (8 pages).
International Search Report and Written Opinion dated Jul. 6, 2015, in International Application No. PCT/EP2014/079184 (20 pages.).
Panagiotis M. Angelopoulos et al., "Production of durable expanded perlite microspheres in a Vertical Electrical Furnace;" 2016 IOP Conference Series: Materials Science and Engineering 123 (2016) 012061; pp. 1-6.
Talc—Cosmetic Grade—Imperial 1885L USP BC, Brenntag Specialties, Product Data Sheet [online], Dec. 2016, Issued on Feb. 2004, [retrieved on May 12, 2017], Retrieved from the Internet, URL, http://www.brenntag.com/media/documents/bsi/product_data_sheets/life_science/bsi_high_purity_talcs/bsi_imp1885l_talc_pds.pdf (cited as a reference which discloses a well-known technology) (1 page).
Toko Perlite Industries Co., Ltd. Product information page [online], May 15, 2017, [retrieved on May 15, 2017], Retrieved from the Internet, URL, http://www.toko-perlite.co.jp/products.html (cited as a reference which discloses a well-known technology) (3 pages).

* cited by examiner

PERSONAL CLEANSING COMPOSITIONS COMPRISING EXPANDED PERLITE MICROSPHERES

This is a continuation of application Ser. No. 15/107,396, filed Jun. 22, 2016, which is a 371 National Stage Application of PCT/EP2014/079184, filed Dec. 23, 2014, and claims foreign priority to EP 13290330.3, filed Dec. 23, 2013, EP 13290329.5, filed Dec. 23, 2013, and EP 14290134.7, filed May 2, 2014, all of which are incorporated herein by reference.

TECHNICAL FIELD

The present invention is related to: (i) a personal care composition comprising a cosmetically acceptable base and inorganic particulate material, for example, a shower gel or hair shampoo, and to a method of making the personal care composition; (ii) a cleaning composition comprising a base and inorganic particulate material, for example, a hard surface cleansing composition and to a method of making the cleaning composition; and (iii) a composition, for example, a personal care composition, the use of an inorganic particulate material having a $d_{50}$ of from about 0.1 µm to about 200 µm in such a composition, and to a method for making such a composition.

BACKGROUND OF THE INVENTION

It is known to add particulate matter to skin cleansing compositions, such as shower gel and bath gels, in order to impart a scrub feel and to aid exfoliation of the uppermost layer of skin upon lathering. More recently, there has been a growing trend to incorporate plastic micro-beads into skin cleansing compositions. However, plastic micro-beads have been found to enter the water course and end up in lakes, seas and oceans. This has led to some environmental groups to call for a ban on plastic micro-beads. Thus, there is ongoing need to develop new and even improved particulates for use in shower gels and the like, which do not suffer from the purported environmental drawbacks of plastic micro-beads.

Further, scouring compositions such as particulate compositions or liquid (incl. gel, paste-type) compositions containing abrasive components are well known in the art. Such compositions are used for cleaning a variety of surfaces; especially those surfaces that tend to become soiled with difficult to remove stains and soils.

Amongst the currently known scouring compositions, the most popular ones are based on abrasive particles with shapes varying from spherical to irregular. The most common abrasive particles are either inorganic like carbonate salt, clay, silica, silicate, shale ash, and quartz sand or organic polymeric beads like polypropylene, PVC, melamine, urea, polyacrylate and derivatives, and come in the form of liquid composition having a creamy consistency with the abrasive particles suspended therein.

Due to the presence of very hard abrasive particles, these compositions can damage, i.e., scratch, the surfaces onto which they have been applied. Indeed, the formulator needs to choose between good cleaning performance but featuring strong surface damage or compromising on the cleaning performance while featuring acceptable surface safety profile. In addition, such currently known scouring compositions at least in certain fields of application (e.g., hard surface cleaning) are perceived by consumers as outdated, and are often disliked due to unpleasant feel on the hands during usage. Abrasive particles derived from natural material such as nut shells e.g. walnut and almond or derived from seed pits e.g. apricot and cherry are sometimes meeting above mentioned requirements, however, they appear in nature with dark color and their inclusion in a cleaning product yield an unaesthetic muddy-like liquid composition. This is highly undesirable by consumer/users because it compromises the aspect of the liquid composition and its cleaning performance. Therefore, there is a real need to identify an abrasive particle derived from a natural material that fulfills equally the aesthetic and performance requirements for cleaning liquid composition.

Moreover, cleansing compositions such as personal care products and washing-up fluids are many and various. There is an ongoing need to develop new products having modified or improved properties which may enhance the cleansing function of the composition and/or provide an enhanced experience for the user, particularly when using personal care products such as hair shampoo and shower/bath gels. For example, the user may prefer a personal care product which generates more foam, or has a creamier texture.

SUMMARY OF THE INVENTION

First General Aspect

According to a first aspect, the present invention is directed to a personal care cleansing composition comprising: a cosmetically acceptable base; and an inorganic particulate material selected from the group consisting of perlite, vermiculite, alumina, nepheline and mixtures thereof. In certain embodiments, the personal care cleansing composition is a shower or bath gel. In certain embodiments, the personal care cleaning composition is an anti-dandruff shampoo.

According to a second aspect, the present invention is directed to a packaged product suitable for commerce comprising the personal care cleansing composition according to the first aspect of the present invention.

According to a third aspect, the present invention is directed to the use of an inorganic particulate material as defined in accordance with the first aspect of the present invention in a personal care cleansing composition comprising a gel, for example, a shower gel.

According to a fourth aspect, the present invention is directed to the use of an inorganic particulate as defined in accordance with the first aspect of the present invention in a hair shampoo, for example, an anti-dandruff shampoo.

According to a fifth aspect, the present invention is directed to a method of treating or preventing dandruff, said method comprising administering by topical application an effective amount of a hair shampoo according to embodiments of the first aspect of the present invention such that dandruff is treated or prevented.

According to a sixth aspect, the present invention is directed to a hair shampoo according to embodiments of the first aspect of the present invention for use in treating or preventing dandruff.

According to a seventh aspect, the present invention is directed to a method for making a personal care cleansing composition according to the first aspect of the present invention, said method comprising combining a cosmetically acceptable base and inorganic particulate material as defined in accordance with the first aspect of the present invention.

Second General Aspect

According to a first aspect, the present invention is directed to a cleaning composition comprising: a base; and an inorganic particulate material selected from the group consisting of spherical perlite, alumina (e.g., spherical alumina), vermiculite, nepheline and mixtures thereof. In certain embodiments, the cleaning composition is a hard surface or tableware cleansing composition.

According to a second aspect, the present invention is directed to a packaged product suitable for commerce comprising the cleaning composition according to the first aspect of the present invention.

According to a third aspect, the present invention is directed to the use of an inorganic particulate material as defined in accordance with the first aspect of the present invention in a cleaning composition comprising a gel, for example, a hard surface cleansing composition.

According to a fourth aspect, the present invention is directed to a cleaning composition including an inorganic particulate material to provide scrubbing action.

According to a fifth aspect, the present invention is directed to a method for making a cleaning composition according to the first aspect of the present invention, said method comprising combining a base and inorganic particulate material as defined in accordance with the first aspect of the present invention.

Third General Aspect

According to a first aspect, the present invention is directed to a composition comprising a base, a foaming agent and inorganic particulate material having a $d_{50}$ of from about 0.1 µm to about 200 µm.

According to a second aspect, the present invention is directed to the use of an inorganic particulate material having a $d_{50}$ of from about 0.1 µm to about 200 µm, in a composition comprising a base and foaming agent, for increasing the foam volume of the composition upon or during topical application of the composition.

According to a third aspect, the present invention is directed to the use of an inorganic particulate material having a $d_{50}$ of from about 0.1 µm to about 200 µm, in a composition comprising a base and foaming agent, for reducing the average bubble size of the foam generated upon or during topical application of the composition.

According to a fourth aspect, the present invention is directed to a method for making a composition according to the first aspect, said method comprising combining a base, foaming agent and inorganic particulate material in suitable amounts.

BRIEF DESCRIPTION OF THE DRAWINGS

FIGS. 1 to 4 relate to the first general aspect.

FIG. 5 relates to the third general aspect.

DETAILED DESCRIPTION OF THE INVENTION

First General Aspect

Figure 1:
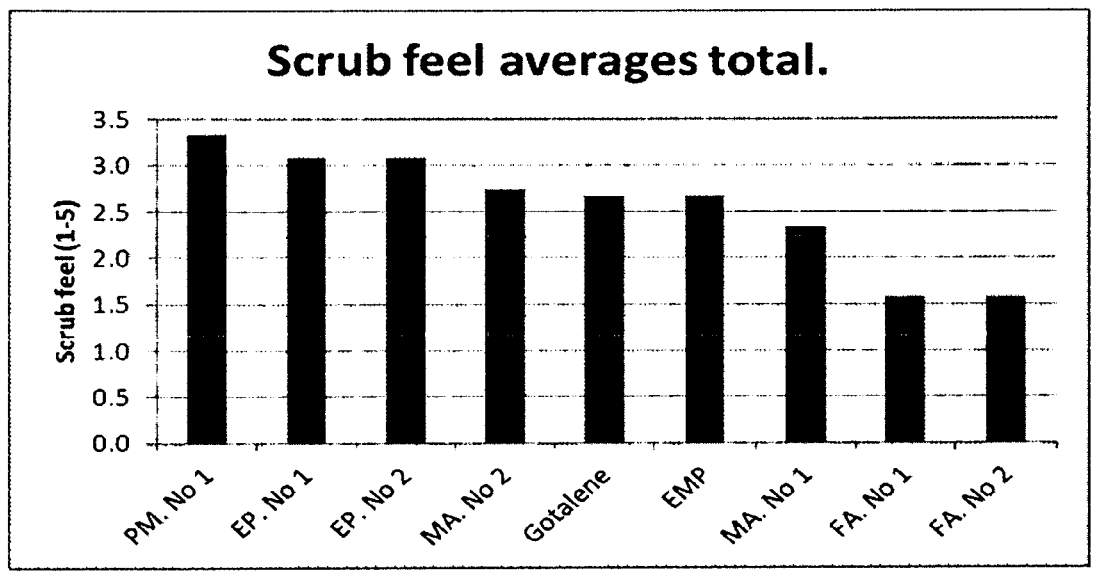
FIG. 1 is a graph summarising the scrub feel of a number of tested gel compositions, as detailed in the Examples.

The term "personal care cleansing composition" used herein means a composition which is compatible with the skin and/or hair, particularly the keratin-containing material making up the outer (uppermost) layer of human skin. In certain embodiments, the personal care cleansing composition is a shower gel or bath gel. In certain embodiments, the personal care cleansing composition is a shower gel. In certain embodiments, the personal care cleansing composition is a hair shampoo, for example, on anti dandruff hair shampoo.

The term "shower gel" or "bath gel" as used herein means a composition comprising a gel of water and detergent bases (e.g., liquid soap). In certain embodiments, it s pH balanced for use on the body. The shower or bath gel may have added functional ingredients such as moisturizer/conditioner, pearlescent s, colorants, fragrance, etc., as described herein. These compositions are used skin cleansing agents in the shower or bath. The pH range for shower and bath gels is typically from about 5.75 to about 7. In contrast, a hair shampoo may be characterized as a composition typically comprising harsher surfactants to clean hair and may be slightly more acidic than a shower or bath gel. A shampoo may be formulated for specific hair conditions such as dryness, oiliness, damage from color treatment and frizziness, etc. Each function may use a different mixture of ingredients which are formulated depending on the target function. The pH range for hair shampoo is typically from about 5 to about 7. Most shampoos typically have a lower pH, e.g., from about 5.5 to about 6, than a shower or bath gel, to match the hairs' natural acidity of about 4.5 to about 5.5.

In certain embodiments, the personal care cleansing composition is not a cream and/or not a lotion and/or not a hair shampoo other than an anti-dandruff shampoo.

The term "gel" used herein includes a phase having gel-like properties, such as low or negligible flow on standing, or a liquid phase of low viscosity. For instance, a gel may be a colloidal suspension of solids dispersed in a liquid or a sol. In certain embodiments, the gel has a Brookfield viscosity of at least about 0.5 Pa·s (at 100 rpm RV spindle 6) and optionally no greater than about 100 Pa·s (at 1 rpm RV spindle 6). Additionally or alternatively, the gel may have a specific gravity ranging from about 0.9 to about 1.2, for example, from about 1.0 to about 1.1. In certain embodiments, the gel is an emulsion of water and detergent base. The detergent base may comprise a surfactant or mixture of surfactants, as described herein. In certain embodiments, the gel may be thixotropic, i.e., gel-like at rest but fluid when agitated (e.g., shaken or squeezed).

In certain embodiments, the shower or bath gel has a scrub feel at least as good as, or even better than, a comparable bath or shower gel comprising polyethylene microbeads, for example, a comparable bath or shower gel comprising Gotalene® 135 colourless 26 micro-beads, available from Du Pont. Said micro-beads are composed of low density polyethylene (LDPE) and characterised in having a maximum particle size of less than 630 µm, a melting point of 106° C., a melt-flow index (190° C./2.16 kg) of 70, a bulk density of >=23, and a specific gravity of 0.918 g/cm³. By "comparable" is meant that the shower gel or bath gel differs only in that the inorganic particulate material is replaced by said micro-beads. A suitable test for scrub feel is described below in the Examples.

In certain embodiments, the hair shampoo comprising the inorganic particulate material provides or aids improved exfoliation of the skin of the scalp when topically applied by massaging into the hair and scalp during washing. In certain embodiments in which the hair shampoo is an anti-dandruff shampoo, the combination of anti-dandruff chemical(s) and inorganic particulate material provides a synergistic improvement in treating dandruff. Without wishing to be bound by theory, it is believed that the exfoliating effect of the inorganic particulate mechanically improves the reduction or elimination of dandruff during washing of the hair.

The personal care cleansing composition (e.g., shower gel or bath gel or hair shampoo) may be provided in a packaged product suitable for commerce (e.g., tub, tube, bottle, packet, sachet, canister, dispenser, and the like).

The Inorganic Particulate Material

Surprisingly, it has been found that inorganic particulate materials in accordance with the first aspect of the invention provide a scrub feel and/or exfoliating properties when included in a personal care cleansing composition comprising a gel, as a partial or total replacement for plastic micro-beads currently used in shower and bath gels. In certain embodiments, the inorganic particulate material has been found to be mildly abrasive. The mechanical action of the application provides an initial scrub feel, then aids exfoliation of the upper layer of skin. In certain embodiments described herein, the inorganic particulate is in the form of spheres or microspheres which are substantially hollow. In such embodiments, following the initial scrub feel, continued mechanical action breaks down the hollow spheres or microspheres further enhancing exfoliation of the upper layer of the skin.

The inorganic particulate material is selected from the group consisting of perlite, vermiculite, alumina, nepheline and mixtures thereof.

In certain embodiments, the inorganic particulate material is selected from the group consisting of perlite, vermiculite, nepheline and mixtures thereof.

In certain embodiments, the inorganic particulate material does not include or is not alumina.

In certain embodiments, the inorganic particulate material comprises, consists essentially of, or consists of: (i) perlite; or (ii) alumina; or (iii) vermiculite; or (iv) nepheline.

In certain embodiments in which the inorganic particulate material comprises, consists essentially of, or consists of, perlite, the perlite is substantially spherical perlite. By "substantially spherical" is meant that individual particles of the inorganic particulate material have a generally (but not necessarily geometrically regular) spherical, spheroidal and/or ovoidal morphology, i.e., generally non-angular, as viewed using an optical microscope (e.g., a Keyence VHX-1000). For example, a substantially spherical particle may have a roundness of 1.15 or less, or 1.10 or less, or 1.05 or less. The roundness of a particulate may be determined in accordance with the following method. An image of the particulate sample is taken using an optical microscope (e.g., a Keyence VHX-100) on a contrasting background. The image is then transferred and opened using Leica LAS Image Analysis Software by Leica Microsystems, Solms, Germany (see: http://www.leica-microsystems.com/products/microscope-software/materials-sciences/details/product/leica-las-image-analysis/downloads/). A sample of about 100 particles is then drawn around and the roundness calculated by the software.

In certain embodiments, the perlite is expanded perlite. Typically, expanded perlite includes one or more cells, or parts of cells, in which a cell is a void space partially or entirely surrounded by walls of glass, usually formed from expansion of gases when the glass is in the softened state. Processes for expanding perlite are well known in the art, and include heating perlite in air to a temperature of least about 700° C., typically between 800° C. and 1100° C., in an expansion furnace. Exemplary processes for producing expanded perlite are described in US-A-20060075930, the entire contents of which is hereby incorporated by reference. Expanded perlite typically has a bulk volume up to 20 times that of the unexpanded material. In certain embodiments, the substantially spherical perlite is expanded perlite.

In certain embodiments, the perlite is in the form of microspheres. The microspheres may be hollow or solid. In certain embodiments, the microspheres are hollow, for example, substantially closed and hollow. In certain embodiments, the microspheres are substantially closed cell structures, e.g., sealed cavities normally filled with air. In certain embodiments, at least 50 wt. % of the perlite is in the form of microspheres, for example, at least about 60 wt. %, or at least about 70 wt. %, or at least about 80 wt. %, or at least about 90 wt. %, or at least about 95 wt. %, or at least about 99 wt. %, or substantially 100 wt. % of the perlite is in the form of microspheres. Perlite in the form of microspheres can be formed in accordance with the methods described in WO-A-2013053635, the entire contents of which is hereby incorporated by reference. Generally, in this process, perlite ore and propellant is fed into an upright furnace and falls along a drop section through multiple heating zones in a furnace shaft of the furnace. The perlite ore is heated to a critical temperature at which the surfaces of the perlite plasticize and perlite grains are expanded on the basis of the propellant.

In certain embodiments, the perlite, be it spherical, expanded, expanded spherical or expanded microspherical, is not milled, i.e., the perlite is not an expanded milled perlite.

In certain embodiments, the inorganic particulate material comprises, consists essentially of, or consists of alumina, optionally excluding non-spherical and non-microspherical fused alumina having a density of greater than about 3.9 g/cc. In certain embodiments, the alumina is of high purity, typically comprising at least about 95.0% alumina by chemical analysis, or at least about 98.0% alumina, or at least about 98.5% alumina, or at least about 99.0% alumina, or at least about 99.5% alumina.

In certain embodiments in which the inorganic particulate material comprises, consists essentially of, or consists of, alumina, the alumina is substantially spherical alumina.

In certain embodiments, the alumina is in the form of microspheres, which may be substantially closed and hollow. In certain embodiments, at least 50 wt. % of the alumina is in the form of microspheres, for example, at least about 60 wt. %, or at least about 70 wt. %, or at least about 80 wt. %, or at least about 90 wt. %, or at least about 95 wt. %, or at least about 99 wt. %, or substantially 100 wt. % of the alumina is in the form of microspheres. An exemplary microspherical alumina is Alodur® bubble alumina, available from Imerys Fused Minerals. Microspherical alumina, also sometimes referred to as alumina bubbles, can be produced by various methods known in the art.

In certain embodiments, the inorganic particulate material and, thus, the skin cleansing composition, is free of crystalline silica.

In certain embodiments, the inorganic particulate material has a $d_{90}$ of no greater than about 500 µm, for example, no greater than about 475 µm, or no greater than about 450 µm, or no greater than about 425 µm, or no greater than about 400 µm, or no greater than about 375 µm, or no greater than about 350 µm, or no greater than about 325 µm, or no greater than about 300 µm, or no greater than about 275 µm, or no greater than about 250 µm, or no greater than about 225 µm, or no greater than about 200 µm.

Unless otherwise specified, the particle size properties referred to herein for the inorganic particulate materials are as measured by the well known conventional method employed in the art of laser light scattering, using a CILAS 1064L particle size analyser, as supplied by CILAS (or by other methods which give essentially the same result). In the laser light scattering technique, the size of particles in powders, suspensions and emulsions may be measured using the diffraction of a laser beam, based on an application of Fraunhofer and Mie theory. Such a machine provides measurements and a plot of the cumulative percentage by volume of particles having a size, referred to in the art as the 'equivalent spherical diameter' (e.s.d), less than given e.s.d values. The mean particle size $d_{50}$ is the value determined in this way of the particle e.s.d at which there are 50% by volume of the particles which have an equivalent spherical diameter less than that $d_{50}$ value. The $d_{10}$ value is the value at which 10% by volume of the particles have an e.s.d less than that $d_{10}$ value. The $d_{90}$ value is the value at which 90% by weight of the particles have an e.s.d less than that $d_{90}$ value. The $d_{100}$ value is the value at which 100% by volume of the particles have an e.s.d less than that $d_{100}$ value. The $d_0$ value is the value at which 0% by volume of the particles have an e.s.d less than that $d_0$ value. Thus, the $d_0$ measurement provides a measure of the smallest particles in any given sample (within the limits of measurement of the particle size analyzer).

In certain embodiments, the inorganic particulate material has a $d_{10}$ of at least about 10 µm, for example, at least about 20 µm, or at least about 30 µm, or at least about 40 µm, or at least about 50 µm, or at least about 75 µm, or at least about 80 µm, or at least about 85 µm, or at least about 90 µm, or at least about 95 µm, or at least about 100 µm.

In certain embodiments, the inorganic particle material has a $d_{10}$ of at least about 30 µm and a $d_{90}$ of no greater than about 500 µm, for example, a $d_{10}$ of at least about 50 µm and a $d_{90}$ of no greater than about 500 µm, or a $d_{10}$ of at least about 50 µm and a $d_{90}$ of no greater than about 475 µm, or a $d_{10}$ of at least about 75 µm and a $d_{90}$ of no greater than about 475 µm, or a $d_{10}$ of at least about 90 µm and a $d_{90}$ of no greater than about 475 µm, or a $d_{10}$ of at least about 90 µm and a $d_{90}$ of no greater than about 450 µm. In said embodiments, the inorganic particulate material may have a $d_{50}$ of from about 150 µm to about 350 µm, for example, from about 150 µm to about 250 µm, or from about 150 µm to about 200 µm, or from about 175 µm to about 300 µm, or from about 175 µm to about 250 µm, or from about 200 µm to about 300 µm, or from about 200 µm to about 275 µm, or from about 225 µm to about 275 µm, or from about 250 µm to about 350 µm, or from about 275 µm to about 325 µm.

In certain embodiments, the inorganic particulate material has a $d_{100}$ of no greater than about 500 µm. In certain embodiments, the inorganic particulate material has a $d_0$ of at least about 1 µm, or at least about 5 µm, or at least about 10 µm.

Any particular particle size distribution may be obtained using conventional methods known in the art, e.g., by screening. For example, screening may be carried out using an Alpine A-200 jet sieve, supplied by Hosakawa Alpine, Germany, with screens provided by Haver & Bocker. The screen apertures may be selected depending on the particle size distribution required. For example, screens with apertures of 100 µm and 500 µm may be used, particularly if it is desired to remove or significantly reduce oversized particles and undersized particles.

In certain embodiments, the inorganic particulate material has a density of from about 0.10 to about 4.0 g/cc, for example, from about 0.10 to about 3.8 g/cc, or from about 0.10 to about 3.5 g/cc, or from about 0.10 to about 3.2 g/cc, or from about 0.10 to about 3.0 g/cc, or from about 0.10 to about 2.5 g/cc, or from about 0.10 to about 2.0 g/cc, or from about 0.10 to about 1.9 g/cc, or from about 0.10 to about 1.8 g/cc, or from about 0.10 to about 1.7 g/cc, or from about 0.10 to about 1.6 g/cc, or from about 0.10 to about 1.5 g/cc, or from about 0.10 to about 1.4 g/cc, or from about 0.10 to about 1.3 g/cc, or from about 0.10 to about 1.2 g/cc, or from about 0.10 to about 1.1 g/cc, or from about 0.10 to about 1.0 g/cc, or from about 0.10 to about 0.9 g/cc, or from about 0.10 to about 0.8 g/cc, or from about 0.10 to about 0.7 g/cc, or from about 0.10 to about 0.6 g/cc, or from about 0.10 to about 0.5 g/cc, or from about 0.10 to about 0.4 g/cc, or from about 0.20 to about 0.6 g/cc, or from about 0.20 to about 0.5 g/cc, or from about 0.20 to about 0.4 g/cc, or from about 0.25 to about 0.4 g/cc, or from about 0.30 to about 0.4 g/cc.

In certain embodiments, the inorganic particulate material, for example, perlite, has a crush strength of from about 350 KPa to about 5500 KPa. Crush strength is a measure of the pressure required to crush a bed of inorganic particulate material, held within a steel die set, by 30% of its original volume, and may be determined in accordance with the method described below in Example 2. In certain embodiments, the inorganic particulate material, which may comprise, consist essentially of, or consist of microspheres of expanded spherical perlite, has a crush strength of greater than about 1000 KPa, or greater than about 2000, KPa, or greater than about 2500 KPa, or greater than about 3000 KPa, or greater than about 3500 KPa, or greater than about 4000 KPa, or greater than about 4500 KPa, or greater than about 5000 KPa. In certain embodiments, the inorganic particulate material has a crush strength of no greater than about 5250 KPa, or no greater than about 5000 KPa. Without wishing to be bound by theory, it is believed that a higher crush strength may increase the exfoliation properties of the personal care composition.

In certain embodiments, the inorganic particulate material, for example, perlite, has a bulk density of from about 150-500 g/l, for example, from about 200-500 g/l, or from about 250-500 g/l, or from about 300-500 g/l, or from about 350-500 g/l, or from about 400-500 g/l, or from about 450-500 g/l, or from about 150-450 g/l, or from about 150-400 g/l, or from about 150-350 g/l, or from about 150-300 g/l, or from about 150-250 g/l, or from about 150-200 g/l. As used herein, the 'bulk density' of a substance is the value obtained when the mass of the substance is divided by its contained volume, after the substance has been subjected to conditions of free pouring. Bulk may density be determined in accordance with the test method described below in Example 2.

In certain embodiments, the inorganic particulate comprises, or consists essentially of, or consists of microspheres of expanded spherical perlite and having a $d_{10}$ of at least about 50 µm and a $d_{90}$ of no greater than about 500 µm, for example, a $d_{10}$ of at least about 50 µm and a $d_{90}$ of no greater than about 450 µm. In such embodiments, the inorganic particulate (i.e., perlite) may have a density of from about 0.20 to about 0.75 g/cc, for example, from about 0.20 to about 0.50 g/cc. Said inorganic particulate may have a $d_{50}$ of from about 150 µm to about 350 µm, for example, from about 150 µm to about 300 µm, or from about 200 µm to about 300 µm, or from about 225 µm to about 275 µm, or from about 240 µm to about 270 µm.

In certain embodiments, the inorganic particulate comprises, or consists essentially of, or consists of microspheres of alumina, for instance, alumina having a purity of at least 98% alumina by chemical analysis, and having a $d_{10}$ of at least about 100 µm and a $d_{90}$ of no greater than about 450 µm. In such embodiments, the inorganic particulate material (i.e., alumina) may have a density of from about 3.0 to about 3.8 cc/g, for example, from about 3.0 to about 3.2 cc/g, or from about 3.5 to about 3.7 cc/g.

Said inorganic particulate material may have a $d_{10}$ of at least about 130 µm and/or a $d_{90}$ of no greater than about 400 µm, or a $d_{10}$ of at least about 140 µm and a $d_{90}$ of no greater than about 395 µm. Said inorganic particulate material may additionally have a $d_{50}$ of from about 200 µm to about 300 µm, for example, from about 240 µm to about 270 µm, or from about 250 µm to about 260 µm.

In certain embodiments, the inorganic particulate, for example, an inorganic particulate comprising, consisting essentially of, or consisting of microspheres of expanded spherical perlite, has a brightness as determined in accordance with ASTM E313 of from about 65% to about 75%, for example, from about 67% to about 74%, or from about 69% to about 73%.

The personal care cleansing composition comprising inorganic particulate material may be characterised in terms of its abrasiveness. This may be determined by in accordance with the abrasive scrub test method described in the Example. In certain embodiments, the personal care cleansing composition comprising inorganic particulate material has an abrasiveness, expressed as a percentage of gloss retained at 20°, of from about 30% to about 99%, or from about 35% to about 90%, or from about 40% to less than 90%, or from about 50% to about 85%, or from about 60% to about 85%, or from about 70% to about 80%, or from about 80% to about 85%. In certain embodiments, the personal care cleansing composition comprising inorganic particulate material has an abrasiveness of at equal to or greater than about 75%, for example, equal to or greater than about 80%, or equal to or greater than about 85%.

In certain embodiments, the total amount of inorganic particulate material present in the personal care cleansing composition is an amount of from about 0.1 wt. % to about 40 wt. %, based on the total weight of the personal care cleansing composition, for example, from about 0.1 wt. % to about 30 wt. %, or from about 0.1 wt. % to about 20 wt. %, or from about 0.1 wt. % to about 15 wt. %, or from about 0.1 wt. % to about 10 wt. %, or from about 0.1 wt. % to about 9.0 wt. %, or from about 0.2 wt. % to about 8.0 wt. %, or from about 0.3 wt. % to about 7.0 wt. %, or from about 0.4 wt. % to about 6.0 wt. %, or from about 0.5 wt. % to about 5.0 wt. %, or from about 0.5 wt. % to about 4.0 wt. %, or from about 0.5 wt. % to about 3.0 wt. %, or from about 0.5 wt. % to about 2.0 wt. %, or from about 0.75 wt. % to about 5.0 wt. %, or from about 0.75 wt. % to about 3.0 wt. %, or from about 0.75 wt. % to about 2.5 wt. %, or from about 1 wt. % about 3.0 wt. %, or from about 1.5 wt. % to about 5.0 wt. %, or from about 2.0 wt. % to about 10 wt. %, or from about 2.0 wt. % to about 5.0 wt. %, or from about 2.5 wt. % to about 5 wt. %, or from about 3.0 wt. % to about 10 wt. %, or from about 3.0 wt. % to about 8 wt. %.

In certain embodiments, the total amount of inorganic particulate material present in the personal care cleaning composition is an amount of from about 0.5 to about 5.0 wt. %, based on the total weight of the personal care cleansing composition.

Base and Additional Components

In certain embodiments; the cosmetically acceptable base is in the form a liquid, gel, emulsion, lotion or paste. In certain embodiments, the base is a gel. In certain embodiments, the base is a liquid. In certain embodiments, the cosmetically acceptable base comprises or constitutes the components of the composition other than the inorganic particulate material.

Thus, the personal care cleansing composition may contain one or more additional components, as described herein.

In certain embodiments, the personal care cleansing composition will comprise water, which may be present in an amount of from about 10 wt. % to about 95 wt. %, based on the total weight of the personal care cleansing composition, for example, from about 20 wt. % to about 90 wt. %, or from about 30 wt. % to about 90 wt. %, or from about 40 wt. % to about 80 wt. %, or from about 50 wt. % to about 75 wt. %, or from about 50 wt. % to about 70 wt. %. The skilled person will be able to select suitable amounts of water for incorporation in the base, based on the amount of the component in the final composition.

In certain embodiments, the personal care cleansing composition comprises one or more surfactants. As described herein, the one or more surfactants may constitute the detergent base of the gel. The one or more surfactants may be selected from zwitterionic, anionic, non-ionic and amphoteric surfactants, and mixtures thereof.

In certain embodiments, the surfactant(s) are present in the personal care cleansing composition in a total amount ranging from about 1 wt. % to about 60 wt. %, based on the total weight of the personal care cleansing composition, for example, from about 5 wt. % to about 50 wt. %, or from about 5 wt. % to about 30 wt. %. The skilled person will be able to select suitable amounts of surfactant for incorporation in the base, based on the amount of surfactant in the final composition.

Suitable zwitterionic surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative zwitterionics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

Suitable anionic surfactants include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate, sodium lauryl sulfoacetate, sodium cocoyl isethionate, sodium methyl cocoyl taurate and mixtures thereof. The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Suitable non-ionic surfactants include the reaction products of compounds having a hydrophobic group and a reactive hydrogen atom. These include alcohols, acids, amides or alkyl phenols reacted with alkylene oxides, especially ethylene oxide either alone or with propylene oxide. Exemplary non-ionics are $C_6$-$C_{22}$ alkyl phenols-ethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides. Other non-ionics are surfactants based on cocoamide and produced by reacting cocoamide with an alcohol amine, such as ethanolamine. Exemplary non-ionics include cocoamide MEA and cocoamide DEA. Other suitable non-ionics include alkyl polyglucosides such as decyl glucoside, lauryl glucoside and octyl glucoside. Also useful are the alkyl polysaccharides.

Suitable cationic surfactants include, but are not limited, to octenidine dihydrochloride, permanently charged quaternary ammonium surfactants such as alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide and dioctadecyldimethylammonium bromide.

These surfactants serve primarily as a cleansing agent, i.e., constituting or forming part of the detergent component of the composition. These surfactants may comprise up to about 50 wt. % of the composition, based on the total weight of the composition, for example, from about 1 wt. % to about 45 wt. % of the composition, or at least about 5 wt. %, or at least about 10 wt. %, or at least about 15 wt. %, or at least about 20 wt. %, or at least about 25 wt. % of the composition.

In certain embodiments in which the personal care cleansing composition is a hair shampoo, the hair shampoo comprises one or more of sodium laureth sulfate, sodium $C_{14-16}$ olefin sulfonate, sodium lauryl sulfoacetate, sodium cocoyl isethionate, sodium methyl cocoyl taurate, cocoamidopropyl betaine, cocoamide MEA, and mixtures thereof.

In certain embodiments in which the hair shampoo is an anti-dandruff shampoo, the shampoo additionally comprises one or more additives, i.e., chemicals, for treating dandruff. In certain embodiments, the additive for treating dandruff, i.e., anti-dandruff chemical is one or more of zinc pyrithone, a corticosteroid, an imidazole antifungal agent such as, for example, ketoconazole, selenium sulfide, and a hydoxypiridone such as, for example, ciclopirox. In certain embodiments, the anti-dandruff chemical comprises or is zinc pyrithone. In certain embodiments, the anti-dandruff chemical comprises or is ketoconazole. The anti-dandruff chemical may be used in a suitable, e.g., effective, amount. Suitable amounts may range from about 0.1 wt. % to about 5 wt. %, based on the total weight of the hair shampoo, for example, from about 0.1 wt. % to about 3 wt. %, or from about 0.1 wt. % to about 2 wt. %. The skilled person will be able to select suitable amounts of anti-dandruff chemical(s) for incorporation in the base, based on the amount of anti-dandruff chemical(s) in the final composition.

In certain embodiments, the shampoo comprises conditioning (anti-static) surfactants to soothe the scalp after washing with the anti-dandruff shampoo. Exemplary conditioning surfactants are hydroxypropyltrimonium chloride and polyglycerol laurate.

In certain embodiments, the personal care cleansing composition comprises one or more thickening agents or suspending agents (e.g., rheology modifier). Such agents may enhance the stability of the inorganic particulate material dispersed throughout the gel. Suitable thickening agents include water soluble/dispersable polymers, which may be cationic, anionic, amphoteric or non-ionic with molecular weights typically greater than about 100,000 Daltons. Such agents may also serve to increase the viscosity of the personal care cleansing composition. Exemplary thickening or suspending agents include carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers; cationic polymer such as modified polysaccharides; cationic modified cellulose; synthetic cationic polymer; cationic starches; cationic galactomannans; and high molecular weight polyethylene glycols, esters of ethylene glycol or esters of polyethylene glycol. Other suitable thickening/suspending agents include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters.

A thickening agent or suspending agent, such as a rheology modifier, when present, may be present in a total amount of from about 0.1 wt. % to about 50 wt. % by weight, based on the total weight of the personal care cleansing composition, for example, from about 0.1 wt. % to about 35 wt. %, or from about 0.1 wt. % to about 20 wt. %, or from about 0.1 wt. % to about 10 wt. %, or from about 0.1 wt. % to about 5 wt. %. The skilled person will be able to select suitable amounts of each component for incorporation in the base, based on the amount of the component in the final composition.

The personal care cleansing composition may contain other components conventionally found in cosmetic applications for skin and hair, including, without limitation, skin conditioning/moisturizing agents, hair conditioning/moisturising agents perfumes, fragrances, opacifiers, pearlescing agents, colourings, preservatives, chelating agents, humectants, herb and/or plant extracts, essential oils, proteins, pH adjusting agents, and anti-microbials. The total amount of other components may be present in amount of from about 0.1 to about 30 wt. %, based on the total weight of the personal care cleansing composition, for example, from about 0.1 wt. % to about 20 wt. %, or from about 0.1 wt. % to about 15 wt. %, or from about 0.5 wt. % to about 10 wt. %, or from about 1 wt. % to about 10 wt. %, or from about 1 wt. % about 5 wt. %. The skilled person will be able to select suitable amounts of each component for incorporation in the base, based on the amount of the component in the final composition.

A suitable amount of pH adjusting agent may be added, if necessary, to adjust the pH of the composition, particularly if the composition is a personal care composition. For example, as described above, a desirable pH range for shower or bath gels is typically from about 5.75 to 7. A desirable pH for shampoos is slightly wider from about 5 to 7. Most shampoos typically have a lower pH (around 5.5 to 6) than shower gels to match the hairs' natural acidity of around 4.5 to 5.5. Suitable pH adjusting agents in sodium hydroxide, sodium chloride and citric acid.

Method of Making Personal Care Cleaning Composition

Personal care cleansing compositions in accordance with certain embodiments of the present invention may be made by conventional methods of preparing personal care cleansing compositions, e.g., shower gels or anti-dandruff shampoos.

Generally, for gel based compositions, the inorganic particulate materials are incorporated in the gel by combining the gel and inorganic particulate material in suitable amounts. The step of combining may include mixing, for example, shear mixing. Before, during or after incorporation of the inorganic particulate material, any additional components may be added to the gel base. If the gel is an emulsion of surfactant and water, the emulsion will normally be prepared first, followed by combining with the inorganic particulate material and any other additional components.

The gel based cleansing composition may be used in a similar way to conventional exfoliating compositions, i.e., a suitable amount of the composition is applied to wetted or washed skin and the composition massaged on the skin. The initial scrub feel will gradually subside as the composition is worked in.

Generally, for hair shampoos, e.g., anti-dandruff shampoo, the shampoo is formulated by incorporating and combining the inorganic particulate materials and the components of the cosmetically acceptable base in suitable amounts. The step of combining may include mixing, for example, shear mixing. Before, during or after incorporation of the inorganic particulate material, any additional components, such as anti-dandruff chemical(s) may be added to the base. If the cosmetically acceptable base is an emulsion of surfactant and water, the emulsion may be prepared first, followed by combining with the inorganic particulate material and any other additional components, such as the anti-dandruff chemical(s).

Treating Dandruff

The anti-dandruff shampoo may be used in a similar way to conventional anti-dandruff shampoo, i.e., a suitable amount of the composition is topically applied to wetted hair and the composition worked in to the hair and massaged into the scalp. As described herein, the presence of the inorganic particulate material may enhances the exfoliation of the skin of the scalp, serving to reduce or even eliminate dandruff during the washing process. In certain embodiments, the combination of anti-dandruff chemical(s) and inorganic particulate material provides a synergistic improve in treating dandruff, i.e., the anti-dandruff properties of the hair shampoo comprising the inorganic particulate material is enhanced compared to a comparable anti-dandruff shampoo absent the inorganic particulate material. In certain embodiments, the amount of anti-dandruff chemical(s) effective to treat or prevent dandruff may be reduced when the inorganic particulate material is utilised in the hair shampoo.

As such, in certain embodiments, there is provided a method of treating or preventing dandruff in a subject (e.g., a mammalian subject, such as a human), said method comprising administering by topical application an effective amount of a hair shampoo as describe herein such that dandruff is treated or prevented. The hair shampoo may topically applied over a period of time, for example, over a week, or two weeks, or three weeks, or a calendar month or months (e.g., two, three, four, five, six, seven, eight, nine, ten, eleven months) or over a year or more than a year, e.g., two years, or three, years, or four years, or five years). The hair shampoo applied daily over the period of time, or applied every other day over the period of time, or applied tri-weekly over the period of time, or applied twice weekly over the period of time, or applied weekly over the period of time.

For the avoidance of doubt, the present application is directed to the subject-matter described in the following numbered paragraphs:

1. A personal care cleansing composition comprising:
   a cosmetically acceptable base; and
   an inorganic particulate material selected from the group consisting of perlite, vermiculite, alumina, nepheline and mixtures thereof.

2. The personal care cleansing composition according to numbered paragraph 1, wherein the inorganic particulate material is perlite and the perlite is a spherical perlite.

3. The personal care cleansing composition according to numbered paragraph 1 or 2, wherein the perlite or spherical perlite is expanded perlite, optionally wherein the expanded perlite has not been milled.

4. The personal care cleansing composition according to numbered paragraph 2 or 3, wherein the spherical perlite comprises microspheres, for example, wherein at least 80 wt. % of the spherical perlite is microspheres.

5. The personal care cleansing composition according to numbered paragraph 4, wherein the microspheres are substantially closed and hollow.

6. The personal care cleansing composition according to any preceding numbered paragraph, wherein the inorganic particulate has a $d_{90}$ of no greater than about 500 µm, for example, no greater than about 400 µm.

7. The personal care cleansing composition according to numbered paragraph 6, wherein the inorganic particulate material has a $d_{10}$ of at least about 30 µm and a $d_{90}$ of no greater than about 500 µm, for example, a $d_{10}$ of at least about 30 µm and a $d_{90}$ of no greater than about 400 µm.

8. The personal care cleansing composition according to any preceding numbered paragraph, wherein the inorganic particulate material has a density of from about 0.10 to about 4.0 g/cc.

9. The personal care cleansing composition according to any preceding numbered paragraph, wherein the inorganic particulate material has a density of from about 0.10 to about 2.0 g/cc, for example, from about 0.10 to about 1.0 g/cc.

10. The personal care cleansing composition according to numbered paragraph 9, wherein the inorganic particulate material has a density of from about 0.20 to about 0.50 g/cc.

11. The personal care cleansing composition according to numbered paragraph 1, wherein the inorganic particulate comprises, or consists essentially of, or consists of, microspheres of expanded spherical perlite and having a $d_{10}$ of at least about 50 µm and a $d_{90}$ of no greater than about 450 µm, and optionally a density of from about 0.20 to about 0.50 g/cc.

12. The personal care cleansing composition according to numbered paragraph 11, wherein the inorganic particulate has a $d_{10}$ of at least about 150 µm, for example, at least about 180 µm, and optionally a $d_{50}$ of from about 220 µm to about 280 µm.

13. The personal care cleansing composition according to numbered paragraph 11, wherein the inorganic particulate material has a $d_{10}$ of at least about 10 µm, for example, at least about 80 µm, and a $d_{90}$ of no greater than about 450 µm, for example, no greater than about 300 µm.

14. The personal care cleansing composition according to numbered paragraph 1, wherein the inorganic particulate comprises, or consists essentially of, or consists of, microspheres of alumina and having a $d_{10}$ of at least about 100 µm and a $d_{90}$ of no greater than about 450 µm, and optionally a density of from about 3.0 to about 3.8 g/cc.

15. The personal care cleansing composition according to numbered paragraph 14, wherein the inorganic particulate material has a $d_{10}$ of at least about 130 µm and/or a $d_{90}$ of no greater than about 400 µm, or a $d_{10}$ of at least about 140 µm and a $d_{90}$ of no greater than about 395 µm.

16. The personal care cleansing composition according to any preceding numbered paragraph, wherein the inorganic particulate is present in an amount of from about 0.1 wt. % to about 20 wt. %, based on the total weight of the personal care cleansing composition, optionally wherein the personal care cleansing composition comprises from about 1 wt. % to about 60 wt. % surfactant, water and optional additional components other than surfactant.

17. The personal care cleansing composition according to numbered paragraph 16, wherein the inorganic particulate is present in an amount of from about 0.5 wt. % to about 5 wt. %.

18. The personal care cleansing composition according to any preceding numbered paragraph, further comprising one or more of: surfactant(s), thickening agent(s), suspending agent(s), skin conditioning/moisturising agent(s), hair conditioning/moisturising agent(s), perfume(s), fragrance(s), opacifier(s), pearlescing agent(s), colouring(s), preservative(s), chelating agent(s), humectants(s), herb and/or plant extract(s), essential oil(s), protein(s), pH adjusting agent(s), and anti-microbial(s).

19. The personal care cleansing composition according to any preceding numbered paragraph, wherein the cosmetically acceptable base is a gel.

20. The personal care cleansing composition according to numbered paragraph 19, wherein the skin cleansing composition is a shower gel or bath gel.

21. The personal care cleansing composition according to any one of numbered paragraphs 1-18, wherein the personal care composition is a hair shampoo, for example, an antidandruff shampoo, and the cosmetically acceptable base comprises components suitable for use in a hair shampoo.

22. A packaged product suitable for commerce comprising the personal care cleansing composition according to any one of numbered paragraphs 1-21.

23. Use of an inorganic particulate material as defined in any one of numbered paragraphs 1-17 in a personal care cleansing composition comprising a gel, for example, a shower gel.

24. Use according to numbered paragraph 23, wherein the inorganic particulate material provides a scrub feel, skin exfoliation, or both.

25. Use of an inorganic particulate as defined in any one of numbered paragraphs 1-17 in a hair shampoo, for example, an anti-dandruff shampoo.

26. Use according to paragraph 25, wherein the inorganic particulate material aids or provides exfoliation of the skin of the scalp.

27. A method of treating or preventing dandruff, said method comprising administering by topical application an effective amount of a hair shampoo according to numbered paragraph 21 such that dandruff is treated or prevented.

28. A hair shampoo according to numbered paragraph 21 for use in treating or preventing dandruff, optionally wherein the combination of anti-dandruff chemical(s) and inorganic particulate material provides a synergistic improvement in treating dandruff.

29. The method according to numbered paragraph 27 or the hair shampoo for use according to numbered paragraph 28, wherein the hair shampoo is topically applied over a period of time, for example, over a week, or two weeks, or three weeks, or a calendar month.

30. A method for making a personal care cleansing composition according to anyone of paragraphs 1-21, said method comprising combining a cosmetically acceptable base, e.g., a gel, and inorganic particulate material as defined in any one of paragraphs 1-21 in suitable amounts.

Second General Aspect

The term "cleaning composition" used herein means a composition which is compatible with hard surfaces and/or tableware. In certain embodiments, the cleaning composition is a hard surface cleansing composition or tableware cleansing composition. It is an advantage of the compositions according to the present invention that they may be used to clean/cleanse inanimate surfaces made of a variety of materials like glazed and non-glazed ceramic tiles, enamel, stainless steel, Inox®, Formica®, vinyl, no-wax vinyl, linoleum, melamine, glass, plastics, Teflon®, painted surfaces and the like.

The term "hard surface cleansing composition" or "tableware cleansing composition" as used herein means a composition comprising a solid (e.g., a powder), or a liquid, such as a gel of water and bases (e.g., liquid soap). Liquid compositions include compositions having a water-like viscosity as well as thickened compositions, such as gels and pastes.

In certain embodiments herein, the compositions herein are neutral compositions, and thus have a pH, as is measured at 25° C., of 6-8, more preferably 6.5-7.5, even more preferably 7. In other embodiments, the compositions have pH above pH 4 and alternatively have pH below pH 10. In certain embodiments, the cleaning composition has a pH of from 7 to 9, for example, a pH of about 8.

Accordingly, the compositions herein may comprise suitable bases and acids to adjust the pH.

A suitable base to be used herein is an organic and/or inorganic base. Suitable bases for use herein are the caustic alkalis, such as sodium hydroxide, potassium hydroxide and/or lithium hydroxide, and/or the alkali metal oxides such, as sodium and/or potassium oxide or mixtures thereof. In some embodiments, the base is a caustic alkali, more preferably sodium hydroxide and/or potassium hydroxide. Other suitable bases include ammonia, ammonium carbonate, all available carbonate salts such as $K_2CO_3$, $Na_2CO_3$, $CaCO_3$, $MgCO_3$, etc., alkanolamines (as e.g. monoethanolamine), urea and urea derivatives, polyamine, etc.

Typical levels of such bases, when present, are of from 0.01% to 5.0%, preferably from 0.05% to 3.0% and more preferably from 0.1% to 0.6% by weight of the total composition.

The compositions herein may comprise an acid to trim its pH to the required level, despite the presence of an acid, if any, the compositions herein will maintain their neutral to alkaline, preferably alkaline, pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of said acids may be commercially available from BASF under the trade name Sokalan® DCS.

A suitable inorganic acid is selected from the group consisting hydrochloric acid, sulphuric acid, phosphoric acid and a mixture thereof.

A typical level of such an acid, when present, is of from 0.01% to 5.0%, preferably from 0.04% to 3.0% and more preferably from 0.05% to 1.5% by weight of the total composition.

In one embodiment according to the present invention the compositions herein are thickened compositions. Preferably, the liquid compositions herein have a viscosity of up to 7500 cps at 20 s$^{-1}$, more preferably from 5000 cps to 50 cps, yet more preferably from 2000 cps to 50 cps and most preferably from 1500 cps to 300 cps at 20 s$^{-1}$ and 20° C. when measured with a Rheometer, model AR 1000 (Supplied by TA Instruments) with a 4 cm conic spindle in stainless steel, 2° angle (linear increment from 0.1 to 100 sec$^{-1}$ in max. 8 minutes).

In another embodiment according to the present invention the compositions herein have a water-like viscosity. By "water-like viscosity" it is meant herein a viscosity that is close to that of water. Preferably the liquid compositions herein have a viscosity of up to 50 cps at 60 rpm, more preferably from 0 cps to 30 cps, yet more preferably from 0 cps to 20 cps and most preferably from 0 cps to 10 cps at 60 rpm and 20° C. when measured with a Brookfield digital viscometer model DV II, with spindle 2.

The term "gel" used herein includes a phase having gel-like properties, such as low or negligible flow on standing, or a liquid phase of low viscosity. For instance, a gel may be a colloidal suspension of solids dispersed in a liquid or a sol. In certain embodiments, the gel has a Brookfield viscosity of at least about 0.5 Pa·s (at 100 rpm RV spindle 6) and optionally no greater than about 100 Pa·s (at 1 rpm RV spindle 6). Additionally or alternatively, the gel may have a specific gravity ranging from about 0.9 to about 1.2, for example, from about 1.0 to about 1.1. In certain embodiments, the gel is an emulsion of water and detergent base. The detergent base may comprise a surfactant or mixture of surfactants, as described herein. In certain embodiments, the gel may be thixotropic, i.e., gel-like at rest but fluid when agitated (e.g., shaken or squeezed).

The cleaning composition (e.g., hard surface cleansing composition or tableware cleansing composition) may be provided in a packaged product suitable for commerce (e.g., tub, tube, bottle, packet, sachet, canister, dispenser, and the like).

The Inorganic Particulate Material

Surprisingly, it has been found that inorganic particulate materials in accordance with the first aspect of the invention provide gentle scrubbing action properties when included in a cleaning composition. In certain embodiments, the inorganic particulate material has been found to be mildly abrasive. In certain embodiments described herein, the inorganic particulate is in the form of spheres or microspheres which are substantially hollow. In certain embodiments, continued mechanical action breaks down the hollow spheres or microspheres further enhancing the gentle scrubbing action of the cleaning composition.

In certain embodiments, the inorganic particulate material is selected from the group consisting of spherical perlite, alumina (e.g., spherical alumina), vermiculite, nepheline and mixtures thereof.

In certain embodiments, the inorganic particulate material comprises, consists essentially of, or consists of: (i) spherical perlite; or (ii) alumina (e.g., spherical alumina); or (iii) vermiculite; or (iv) nepheline.

In certain embodiments, the inorganic particulate material is selected from the group consisting of spherical perlite, alumina, and mixtures thereof.

In certain embodiments, the inorganic particulate material is selected from the group consisting of spherical perlite, spherical alumina, and mixtures thereof.

In certain embodiments in which the inorganic particulate material comprises, consists essentially of, or consists of spherical perlite. By "spherical" is meant that individual particles of the inorganic particulate material have a generally (but not necessarily geometrically regular) spherical, spheroidal and/or ovoidal morphology, i.e., generally non-angular, as viewed using an optical microscope (e.g., a Keyence VHX-1000). For example, a spherical particle may have a roundness of 1.15 or less, or 1.10 or less, or 1.05 or less. The roundness of a particulate may be determined in accordance with the following method. An image of the particulate sample is taken using an optical microscope (e.g., a Keyence VHX-100) on a contrasting background. The image is then transferred and opened using Leica LAS Image Analysis Software by Leica Microsystems, Solms, Germany (see: http://www.leica-microsystems.com/products/microscope-software/materials-sciences/details/product/leica-las-image-analysis/downloads/). A sample of about 100 particles is then drawn around and the roundness calculated by the software.

In certain embodiments, the spherical perlite is expanded perlite. Typically, expanded perlite includes one or more cells, or parts of cells, in which a cell is a void space partially or entirely surrounded by walls of glass, usually formed from expansion of gases when the glass is in the softened state. Processes for expanding perlite are well known in the art, and include heating perlite in air to a temperature of least about 700° C., typically between 800° C. and 1100° C., in an expansion furnace. Exemplary processes for producing expanded perlite are described in US-A-20060075930, the entire contents of which is hereby incorporated by reference. Expanded perlite typically has a bulk volume up to 20 times that of the unexpanded material.

In certain embodiments, the spherical perlite is in the form of microspheres. The microspheres may be hollow or solid. In certain embodiments, the microspheres are hollow, for example, substantially closed and hollow. In certain embodiments, the microspheres are substantially closed cell structures, e.g., sealed cavities normally filled with air. In certain embodiments, at least 50 wt. % of the perlite is in the form of microspheres, for example, at least about 60 wt. %, or at least about 70 wt. %, or at least about 80 wt. %, or at least about 90 wt. %, or at least about 95 wt. %, or at least about 99 wt. %, or substantially 100 wt. % of the perlite is in the form of microspheres. Perlite in the form of microspheres can be formed in accordance with the methods described in WO-A-2013053635, the entire contents of which is hereby incorporated by reference. Generally, in this process, perlite ore and propellant is fed into an upright furnace and falls along a drop section through multiple heating zones in a furnace shaft of the furnace. The perlite ore is heated to a critical temperature at which the surfaces of the perlite plasticize and perlite grains are expanded on the basis of the propellant.

In certain embodiments, the spherical perlite, be it expanded spherical or expanded microspherical, is not milled, i.e., the spherical perlite is not an expanded milled perlite.

In certain embodiments, the inorganic particulate material comprises, consists essentially of, or consists of alumina (e.g., spherical alumina), optionally excluding non-spherical and non-microspherical fused alumina having a density of greater than about 3.9 g/cc. In certain embodiments, the alumina is of high purity, typically comprising at least about 95.0% alumina by chemical analysis, or at least about 98.0% alumina, or at least about 98.5% alumina, or at least about 99.0% alumina, or at least about 99.5% alumina.

In certain embodiments in which the inorganic particulate material comprises, consists essentially of, or consists of, alumina, the alumina is substantially spherical alumina.

In certain embodiments, the alumina is in the form of microspheres, which may be substantially closed and hollow. In certain embodiments, at least 50 wt. % of the alumina is in the form of microspheres, for example, at least about 60 wt. %, or at least about 70 wt. %, or at least about 80 wt. %, or at least about 90 wt. %, or at least about 95 wt. %, or at least about 99 wt. %, or substantially 100 wt. % of the alumina is in the form of microspheres. An exemplary microspherical alumina is Alodur® bubble alumina, available from Imerys Fused Minerals, Austria. Microspherical alumina, also sometimes referred to as alumina bubbles, can be produced by various methods known in the art.

In certain embodiments, the inorganic particulate material and, thus, the cleaning composition, is free of crystalline silica.

In certain embodiments, the inorganic particulate material has a $d_{90}$ of no greater than about 500 µm, for example, no greater than about 475 µm, or no greater than about 450 µm, or no greater than about 425 µm, or no greater than about 400 µm, or no greater than about 375 µm, or no greater than about 350 µm, or no greater than about 325 µm, or no greater than about 300 µm, or no greater than about 275 µm, or no greater than about 250 µm, or no greater than about 225 µm, or no greater than about 200 µm, no greater than about 175 µm, or no greater than about 150 µm, or no greater than about 125 µm, no greater than about 100 µm.

Unless otherwise specified, the particle size properties referred to herein for the inorganic particulate materials are as measured by the well known conventional method employed in the art of laser light scattering, using a CILAS 1064L particle size analyser, as supplied by CILAS (or by other methods which give essentially the same result). In the laser light scattering technique, the size of particles in powders, suspensions and emulsions may be measured using the diffraction of a laser beam, based on an application of Fraunhofer and Mie theory. Such a machine provides measurements and a plot of the cumulative percentage by volume of particles having a size, referred to in the art as the 'equivalent spherical diameter' (e.s.d), less than given e.s.d values. The mean particle size $d_{50}$ is the value determined in this way of the particle e.s.d at which there are 50% by volume of the particles which have an equivalent spherical diameter less than that $d_{50}$ value. The $d_{10}$ value is the value at which 10% by volume of the particles have an e.s.d less than that $d_{10}$ value. The $d_{90}$ value is the value at which 90% by weight of the particles have an e.s.d less than that $d_{90}$ value. The $d_{100}$ value is the value at which 100% by volume of the particles have an e.s.d less than that $d_{100}$ value. The $d_0$ value is the value at which 0% by volume of the particles have an e.s.d less than that $d_0$ value. Thus, the $d_0$ measurement provides a measure of the smallest particles in any given sample (within the limits of measurement of the particle size analyzer).

In certain embodiments, the inorganic particulate material has a $d_{10}$ of at least about 10 µm, for example, at least about 20 µm, or at least about 30 µm, or at least about 40 µm, or at least about 50 µm, or at least about 75 µm, or at least about 80 µm, or at least about 85 µm, or at least about 90 µm, or at least about 95 µm, or at least about 100 µm.

In certain embodiments, the inorganic particle material has a $d_{10}$ of at least about 10 µm and a $d_{90}$ of no greater than about 500 µm, for example, a $d_{10}$ of at least about 30 µm and a $d_{90}$ of no greater than about 500 µm a $d_{10}$ of at least about 50 µm and a $d_{90}$ of no greater than about 500 µm, or a $d_{10}$ of at least about 50 µm and a $d_{90}$ of no greater than about 475 µm, or a $d_{10}$ of at least about 75 µm and a $d_{90}$ of no greater than about 475 µm, or a $d_{10}$ of at least about 90 µm and a $d_{90}$ of no greater than about 475 µm, or a $d_{10}$ of at least about 90 µm and a $d_{90}$ of no greater than about 450 µm. In said embodiments, the inorganic particulate material may have a $d_{50}$ of from about 25 µm to about 350 µm, for example, from about 50 µm to about 350 µm, or from about 100 µm to about 350µ, or from about 150 µm to about 350 µm, or from about 150 µm to about 250 µm, or from about 150 µm to about 200 µm, or from about 175 µm to about 300 µm, or from about 175 µm to about 250 µm, or from about 200 µm to about 300 µm, or from about 200 µm to about 275 µm, or from about 225 µm to about 275 µm, or from about 250 µm to about 350 µm, or from about 275 µm to about 325 µm, or from about 25 µm to about 100 µm, or from about 30 µm to about 80 µm, or from about 50 µm to about 100 µm, or from about 50 µm to about 75 µm.

In certain embodiments, the inorganic particulate material has a $d_{100}$ of no greater than about 500 µm. In certain embodiments, the inorganic particulate material has a $d_0$ of at least about 1 µm, or at least about 5 µm, or at least about 10 µm.

Any particular particle size distribution may be obtained using conventional methods known in the art, e.g., by screening. For example, screening may be carried out using an Alpine A-200 jet sieve, supplied by Hosakawa Alpine, Germany, with screens provided by Haver & Bocker. The screen apertures may be selected depending on the particle size distribution required. For example, screens with apertures of 100 µm and 500 µm may be used, particularly if it is desired to remove or significantly reduce oversized particles and undersized particles.

In certain embodiments, the inorganic particulate material has a density of from about 0.10 to about 4.0 g/cc, for example, from about 0.10 to about 3.8 g/cc, or from about 0.10 to about 3.5 g/cc, or from about 0.10 to about 3.2 g/cc, or from about 0.10 to about 3.0 g/cc, or from about 0.10 to about 2.5 g/cc, or from about 0.10 to about 2.0 g/cc, or from about 0.10 to about 1.9 g/cc, or from about 0.10 to about 1.8 g/cc, or from about 0.10 to about 1.7 g/cc, or from about 0.10 to about 1.6 g/cc, or from about 0.10 to about 1.5 g/cc, or from about 0.10 to about 1.4 g/cc, or from about 0.10 to about 1.3 g/cc, or from about 0.10 to about 1.2 g/cc, or from about 0.10 to about 1.1 g/cc, or from about 0.10 to about 1.0 g/cc, or from about 0.10 to about 0.9 g/cc, or from about 0.10 to about 0.8 g/cc, or from about 0.10 to about 0.7 g/cc, or from about 0.10 to about 0.6 g/cc, or from about 0.10 to about 0.5 g/cc, or from about 0.10 to about 0.4 g/cc, or from about 0.20 to about 0.6 g/cc, or from about 0.20 to about 0.5 g/cc, or from about 0.20 to about 0.4 g/cc, or from about 0.25 to about 0.4 g/cc, or from about 0.30 to about 0.4 g/cc.

In certain embodiments, the inorganic particulate comprises, or consists essentially of, or consists of microspheres of expanded spherical perlite and having a $d_{10}$ of at least about 10 µm and a $d_{90}$ of no greater than about 150 µm, for example, a $d_{10}$ of at least about 15 µm and a $d_{90}$ of no greater than about 135 µm, or a $d_{10}$ of at least about 20 µm and a $d_{90}$ of no greater than about 115 µm, or a $d_{10}$ of at least about 20 µm and a $d_{90}$ of no greater than about 100 µm. In such embodiments, the inorganic particulate (i.e., perlite) may have a density of from about 0.20 to about 2.50 g/cc, for example, from about 1.00 to about 2.25 g·cc, or from about 1.50 to about 2.25 g/cc, or from about 1.75 to about 2.25 g/cc, or from about 1.80 to about 2.10 g/cc, or from about 1.90 to about 2.00 g/cc. In certain embodiments, a cleaning composition comprising such an inorganic particulate material (i.e., microspheres of expanded spherical perlite) has an abrasiveness (% of gloss at 20°) of at least about 90%, relative to a comparable cleaning composition absent said inorganic particulate material, for example, an abrasiveness of from about 90% to about 97%, or from about 92 to about 96%.

Abrasiveness may be determined in accordance with the method described herein. In such embodiments, the microspheres of expanded spherical perlite may have a $d_{50}$ of from about 25 µm to about 100 µm, or from about 50 to about 75 µm.

In certain embodiments, the inorganic particulate comprises, or consists essentially of, or consists of microspheres of expanded spherical perlite and having a $d_{10}$ of at least about 50 µm and a $d_{90}$ of no greater than about 450 µm, for example, a $d_{10}$ of at least about 70 µm and a $d_{90}$ of no greater than about 420 µm, or a $d_{10}$ of at least about 80 µm and a $d_{90}$ of no greater than about 350 µm, or a $d_{10}$ of at least about 80 µm and a $d_{90}$ of no greater than about 300 µm. In such embodiments, the inorganic particulate (i.e., perlite) may have a density of from about 0.20 to about 1.00 g/cc, for example, from about 0.30 g/cc to about 0.70 g/cc, or from about, or from about 0.35 g/cc to about 0.65 g/cc. Said inorganic particulate may have a $d_{90}$ of from about 150 µm to about 300 µm, for example, from about 150 µm to about 200 µm, or from about 200 µm to about 300 µm, or from about 225 µm to about 275 µm, or from about 240 µm to about 270 µm.

In certain embodiments, the inorganic particulate comprises, or consists essentially of, or consists of microspheres of alumina, for instance, spherical alumina having a purity of at least 98% alumina by chemical analysis, and having a $d_{10}$ of at least about 50 µm, for example, a $d_{10}$ of at least about 100 µm and a $d_{90}$ of no greater than about 450 µm. In such embodiments, the inorganic particulate material (i.e., spherical alumina) may have a density of from about 3.0 to about 3.8 g/cc, for example, from about 3.0 to about 3.5 g/cc, or from about 3.1 to about 3.4 g/cc, or from about 3.0 to about 3.2 g/cc, or from about 3.2 to about 3.4 g/cc, or from about 3.5 to about 3.7 g/cc.

Said inorganic particulate material (i.e., spherical alumina) may have a $d_{10}$ of at least about 130 µm and/or a $d_{90}$ of no greater than about 400 µm, or a $d_{10}$ of at least about 140 µm and a $d_{90}$ of no greater than about 395 µm. Said inorganic particulate material may additionally have a $d_{50}$ of from about 200 µm to about 300 µm, for example, from about 240 µm to about 270 µm, or from about 250 µm to about 260 µm. Said inorganic particulate material may have a $d_{10}$ of at least about 50 µm and/or a $d_{90}$ of no greater than about 250 µm, and may additionally have a $d_{50}$ of from about 100 µm to about 200 µm. For example, the inorganic particulate material may have a $d_{50}$ of at least about 50 µm, a $d_{90}$ of no greater than about 225 µm or even no greater than about 210 µm, and a $d_{50}$ of from about 125 µm to about 175 µm, for example, from about 140 µm to about 160 µm.

The cleaning composition comprising inorganic particulate material may be characterised in terms of its abrasiveness. This may be determined by in accordance with the abrasive scrub test method described in the Example. In certain embodiments, the cleaning composition comprising inorganic particulate material has an abrasiveness, expressed as a percentage of gloss retained at 20°, of from about 30% to about 99%, or from about 35% to about 90%, or from about 40% to less than 90%, or from about 50% to about 85%, or from about 60% to about 85%, or from about 70% to about 80%, or from about 80% to about 85%. In certain embodiments, the cleaning composition comprising inorganic particulate material has an abrasiveness of at equal to or greater than about 75%, for example, equal to or greater than about 80%, or equal to or greater than about 85%, or equal to or greater than about 90%.

In certain embodiments, the total amount of inorganic particulate material present in the cleaning composition is an amount of from about 0.01 wt. % to about 40 wt. %, based on the total weight of the cleaning composition, for example, from about 0.05 wt. % to about 30 wt. %, or from about 0.1 wt. % to about 20 wt. %, or from about 0.1 wt. % to about 15 wt. %, or from about 0.1 wt. % to about 10 wt. %, or from about 0.1 wt. % to about 9.0 wt. %, or from about 0.2 wt. % to about 8.0 wt. %, or from about 0.3 wt. % to about 7.0 wt. %, or from about 0.4 wt. % to about 6.0 wt. %, or from about 0.5 wt. % to about 5.0 wt. %, or from about 0.5 wt. % to about 4.0 wt. %, or from about 0.5 wt. % to about 3.0 wt. %, or from about 0.5 wt. % to about 2.0 wt. %, or from about 0.75 wt. % to about 5.0 wt. %, or from about 0.75 wt. % to about 3.0 wt. %, or from about 0.75 wt. % to about 2.5 wt. %, or from about 1 wt. % about 3.0 wt. %, or from about 1.5 wt. % to about 5.0 wt. %, or from about 2.0 wt. % to about 10 wt. %, or from about 2.0 wt. % to about 5.0 wt. %, or from about 2.5 wt. % to about 5 wt. %, or from about 3.0 wt. % to about 10 wt. %, or from about 3.0 wt. % to about 8 wt. %.

In certain embodiments, the total amount of inorganic particulate material present in the cleaning composition is an amount of from about 0.1 to about 5.0 wt. %, based on the total weight of the cleaning composition, for example, from about 0.5 to about 2.5 wt. %, or from about 0.5 to about 1.5 wt. %.

Base and Additional Components

In certain embodiments, the base is in the form a liquid, gel, emulsion, lotion or paste. In certain embodiments, the base is a gel. In certain embodiments, the base is a liquid. In certain embodiments, the detergent base comprises or constitutes the components of the composition other than the inorganic particulate material.

Thus, the cleaning composition may contain one or more additional components, as described herein.

In certain embodiments, the cleaning composition will comprise water, which may be present in an amount of from about 10 wt. % to about 95 wt. %, based on the total weight of the cleaning composition, for example, from about 20 wt. % to about 90 wt. %, or from about 30 wt. % to about 90 wt. %, or from about 40 wt. % to about 80 wt. %, or from about 50 wt. % to about 75 wt. %, or from about 50 wt. % to about 70 wt. %. The skilled person will be able to select suitable amounts of water for incorporation in the base, based on the amount of the component in the final composition.

In certain embodiments, the cleaning composition comprises one or more surfactants. As described herein, the one or more surfactants may constitute the detergent base of the gel. The one or more surfactants may be selected from zwitterionic, anionic, non-ionic and amphoteric surfactants, and mixtures thereof.

In certain embodiments, the surfactant(s) are present in the cleaning composition in a total amount ranging from about 1 wt. % to about 60 wt. %, based on the total weight of the cleaning composition, for example, from about 5 wt.

% to about 50 wt. %, or from about 5 wt. % to about 30 wt. %. The skilled person will be able to select suitable amounts of surfactant for incorporation in the base, based on the amount of surfactant in the final composition.

Suitable zwitterionic surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative zwitterionics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

Suitable anionic surfactants include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate, sodium lauryl sulfoacetate, sodium cocoyl isethionate, sodium methyl cocoyl taurate and mixtures thereof. The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Suitable non-ionic surfactants include the reaction products of compounds having a hydrophobic group and a reactive hydrogen atom. These include alcohols, acids, amides or alkyl phenols reacted with alkylene oxides, especially ethylene oxide either alone or with propylene oxide. Exemplary non-ionics are $C_6$-$C_{22}$ alkyl phenols-ethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides. Other non-ionics are surfactants based on cocoamide and produced by reacting cocoamide with an alcohol amine, such as ethanolamine. Exemplary non-ionics include cocoamide MEA and cocoamide DEA. Other suitable non-ionics include alkyl polyglucosides such as decyl glucoside, lauryl glucoside and octyl glucoside. Also useful are the alkyl polysaccharides.

Suitable cationic surfactants include, but are not limited to, octenidine dihydrochloride, permanently charged quaternary ammonium surfactants such as alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide and dioctadecyldimethylammonium bromide.

These surfactants serve primarily as a cleansing agent, i.e., constituting or forming part of the detergent component of the composition. These surfactants may comprise up to about 50 wt. % of the composition, based on the total weight of the composition, for example, from about 1 wt. % to about 45 wt. % of the composition, or at least about 5 wt. %, or at least about 10 wt. %, or at least about 15 wt. %, or at least about 20 wt. %, or at least about 25 wt. % of the composition.

In certain embodiments, the cleaning composition comprises from about 2 to about 20 wt. % anionic surfactant and from 0 to 10 wt. % non-ionic surfactant, based on the total weight of the cleaning composition, for example, from about 5 to about 15 wt. % anionic surfactant and from about 0.1 to about 5 wt. % non-ionic surfactant.

In certain embodiments, the cleaning composition comprises one or more thickening agents or suspending agents (e.g., rheology modifier). Such agents may enhance the stability of the inorganic particulate material dispersed throughout the gel. Suitable thickening agents include water soluble/dispersable polymers, which may be cationic, anionic, amphoteric or non-ionic with molecular weights typically greater than about 100,000 Daltons. Such agents may also serve to increase the viscosity of the cleaning composition. Exemplary thickening or suspending agents include carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers; cationic polymer such as modified polysaccharides; cationic modified cellulose; synthetic cationic polymer; cationic starches; cationic galactomannans; and high molecular weight polyethylene glycols, esters of ethylene glycol or esters of polyethylene glycol. Other suitable thickening/suspending agents include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters.

A thickening agent or suspending agent, such as a rheology modifier, when present, may be present in a total amount of from about 0.1 wt. % to about 50 wt. % by weight, based on the total weight of the cleaning composition, for example, from about 0.1 wt. % to about 35 wt. %, or from about 0.1 wt. % to about 20 wt. %, or from about 0.1 wt. % to about 10 wt. %, or from about 0.1 wt. % to about 5 wt. %. The skilled person will be able to select suitable amounts of each component for incorporation in the base, based on the amount of the component in the final composition.

The cleaning composition may contain other components including, without limitation, conditioning/moisturising agents, perfumes, fragrances, opacifiers, pearlescing agents, colourings, preservatives, chelating agents, humectants, herb and/or plant extracts, essential oils, proteins, pH adjusting agents, and anti-microbials. The total amount of other components may be present in amount of from about 0.1 to about 30 wt. %, based on the total weight of the cleaning composition, for example, from about 0.1 wt. % to about 20 wt. %, or from about 0.1 wt. % to about 15 wt. %, or from about 0.5 wt. % to about 10 wt. %, or from about 1 wt. % to about 10 wt. %, or from about 1 wt. % about 5 wt. %. The skilled person will be able to select suitable amounts of each component for incorporation in the base, based on the amount of the component in the final composition.

Method of Making Cleaning Composition

Cleaning compositions in accordance with certain embodiments of the present invention may be made by conventional methods of preparing cleaning compositions, e.g., hard surface cleansing compositions.

Generally, for gel based compositions, the inorganic particulate materials are incorporated in the gel by combining the gel and inorganic particulate material in suitable amounts. The step of combining may include mixing, for example, shear mixing. Before, during or after incorporation of the inorganic particulate material, any additional components may be added to the gel base. If the gel is an emulsion of surfactant and water, the emulsion will normally be prepared first, followed by combining with the inorganic particulate material and any other additional components.

The gel based cleaning composition may be used in a similar way to conventional cleaning compositions, i.e., a suitable amount of the composition is applied to wetted or washed surface and the composition massage.

For the avoidance of doubt, the present application is directed to the subject-matter described in the following numbered paragraphs:

1. A cleaning composition comprising:
a base; and
an inorganic particulate material selected from the group consisting of spherical perlite, alumina, vermiculite, nepheline and mixtures thereof.

2. The cleaning composition according to numbered paragraph 1, wherein the base comprises a detergent.

3. The cleaning composition according to numbered paragraph 1 or 2, wherein the spherical perlite is expanded perlite, optionally wherein the expanded perlite has not been milled.

4. The cleaning composition according to any preceding numbered paragraph, wherein the spherical perlite comprises microspheres, for example, wherein at least 80 wt. % of the spherical perlite is microspheres.

5. The cleaning composition according to numbered paragraph 4, wherein the microspheres are substantially closed and hollow.

6. The cleaning composition according to any preceding numbered paragraph, wherein the inorganic particulate has a $d_{90}$ of no greater than about 500 μm, for example, no greater than about 400 μm.

7. The cleaning composition according to numbered paragraph 6, wherein the inorganic particulate material has a d10 of at least about 10 μm and a d90 of no greater than about 500 μm, for example, a d10 of at least about 10 μm and a d90 of no greater than about 400 μm.

8. The cleaning composition according to any preceding numbered paragraph, wherein the inorganic particulate material has a density of from about 0.10 to about 4.0 g/cc.

9. The cleaning composition according to any preceding numbered paragraph, wherein the inorganic particulate material has a density of from about 0.10 to about 2.0 g/cc, for example, from about 0.10 to about 1.0 g/cc.

10. The cleaning composition according to numbered paragraph 8, wherein the inorganic particulate material has a density of from about 1.50 to about 2.50 g/cc.

11. The cleaning composition according to numbered paragraph 9, wherein the inorganic particulate material has a density of from about 0.20 to about 0.70 g/cc.

12. The cleaning composition according to numbered paragraph 1, wherein the inorganic particulate comprises, or consists essentially of, or consists of, microspheres of expanded spherical perlite and having a d10 of at least about 10 μm and a d90 of no greater than about 450 μm, and optionally a density of from about 0.20 to about 0.70 g/cc or from about 1.50 to about 2.50 g/cc.

13. The cleaning composition according to numbered paragraph 12, wherein the inorganic particulate material has a d50 of from about 180 μm to about 280 μm.

14. The cleaning composition according to numbered paragraph 1, wherein the inorganic particulate material has a d50 of from about 30 μm to about 80 μm.

15. The cleaning composition according to numbered paragraph 1, wherein the inorganic particulate comprises, or consists essentially of, or consists of, microspheres of alumina and having a d10 of at least about 50 μm and a d90 of no greater than about 450 μm, and optionally a density of from about 3.0 to about 3.8 g/cc.

16. The cleaning composition according to numbered paragraph 1, wherein the inorganic particulate material comprises, or consists essentially of, or consists of, microspheres of alumina and having a d50 of at least about 150 μm and/or a d90 of no greater than about 200 μm.

17. The cleaning composition according to any preceding numbered paragraph, wherein the inorganic particulate is present in an amount of from about 0.01 wt. % to about 20 wt. %, based on the total weight of the cleaning composition, optionally wherein the cleaning composition comprises from about 1 wt. % to about 60 wt. % surfactant, water and optional additional components other than surfactant.

18. The cleaning composition according to numbered paragraph 17, wherein the inorganic particulate is present in an amount of from about 0.5 wt. % to about 5 wt. %.

19. The cleaning composition according to any preceding numbered paragraph, further comprising one or more of: surfactant(s), thickening agent(s), suspending agent(s), conditioning/moisturising agent(s), perfume(s), fragrance(s), opacifier(s), pearlescing agent(s), colouring(s), preservative (s), chelating agent(s), humectants(s), herb and/or plant extract(s), essential oil(s), protein(s), pH adjusting agent(s), and anti-microbial(s).

20. The cleaning composition according to any preceding numbered paragraph, wherein the base is a gel.

21. The cleaning composition according to numbered paragraph 1, wherein the cleansing composition is a hard surface cleansing composition or tableware cleansing composition.

22. A packaged product suitable for commerce comprising the cleaning composition according to any one of numbered paragraphs 1-21.

23. Use of an inorganic particulate material as defined in any one of numbered paragraphs 1-18 in a cleaning composition comprising a base, for example, a hard surface cleaning composition, optionally wherein the base is a gel.

24. Use according to numbered paragraph 23, wherein the inorganic particulate material provides a scrubbing action.

25. A method for making a cleaning composition according to anyone of numbered paragraphs 1-21, said method comprising combining a base, e.g., a gel, and inorganic particulate material as defined in any one of paragraphs 1-18 in suitable amounts.

Third General Aspect

In certain embodiments, the composition is a personal care composition, e.g., a personal care product. In other embodiments in which the composition is a personal care composition, the base will be a cosmetically acceptable base. Personal care compositions include, but are not limited to, hair and/or skin cleansing compositions such as shampoo (optionally including conditioner), soap including liquid soaps such as hand-, face- and bodywash, shower gel, bath gel and shaving foam or gel.

In certain embodiments, the composition is a hair shampoo. The hair shampoo may comprise a conditioning/moisturising component.

In certain embodiments, the composition is a shaving gel. In certain embodiments, the composition is a shaving foam. A shaving foam, unlike a shaving gel, comprises a propellant (e.g., butane or propane) which expands and instantly evaporates when the foam is dispensed from its container (e.g., can), filling the foam with bubbles. A shaving gel may be regarded as a post-foaming gel in that the foam is not generated immediately on dispensing the gel, but during application as the gel is massaged into the skin by the user. For instance, the post-foaming gel composition may include one or more or the following: a soap, a volatile liquid post-foaming agent, a silicone copolymer surfactant, water, and a secondary non-ionic surfactant.

In certain embodiments, the composition is a dishwashing preparation, for example, a liquid or gel, such as a washing-up liquid. The dishwashing preparation may or may not comprise a cosmetically acceptable base. In certain embodiments, the base is a cosmetically acceptable base. In certain embodiments, the base will comprise water and detergent, and optionally a fragrance component, and optionally a colourant. In certain embodiments, the dishwashing preparation, e.g., washing-up liquid, is suitable for hand-washing crockery (e.g., plates, dishes and other eating and serving tableware, typically made of some ceramic material, some metallic material, or some plastic material), cutlery, glassware, drinking vessels other than glassware, cookware (e.g., pots, pans, baking trays, etc.) and cooking utensils, and the like.

The composition may further comprise one or more of: thickening agent(s), suspending agent(s), skin conditioning/moisturising agent(s), hair conditioning agent(s), perfume(s), fragrance(s), opacifier(s), pearlescing agent(s), colouring(s), preservative(s), chelating agent(s); humectant(s) herb and/or plant extract(s), essential oil(s), protein(s), pH adjusting agent(s), and anti-microbial(s). These components may comprise up to about 20 wt. % of the composition, based on the total weight of the composition, for example, from about 0.1 wt. % to about 15 wt. %, or from about 1 wt. % to about 10 wt. %, or from about 0.5 wt. % to about 5 wt. % of the composition. The composition may further comprise surfactant(s) other than those of the foaming agent. Such surfactants are understood by those skilled in the art not to have any discernible foaming properties. These surfactants serve primarily as a cleansing agent, i.e., constituting or forming part of the detergent component of the composition. These surfactants may comprise up to about 30 wt. % of the composition, based on the total weight of the composition, for example, from about 1 wt. % to about 30 wt. % of the composition, or at least about 5 wt. %, or at least about 10 wt. %, or at least about 15 wt. %, or at least about 20 wt. %, or at least about 25 wt. % of the composition. As described herein, the one or more components listed above may be comprised within the base of the composition.

The composition (e.g., personal care composition or dishwashing preparation) may be provided in a packaged product suitable for commerce (e.g., tub, tube, bottle, packet, sachet, canister, dispenser, and the like).

In use, the composition may be diluted with an external source of water (e.g., from a tap or showerhead, or from a basin or bath of water) during topical application to the mammalian body (e.g., human body) or article (i.e., crockery, cutlery and the like). Thus, there is provided a diluted composition which is prepared by diluting the composition with from about 1 wt. % to about 99 wt. % of water, for example, from about 5 wt. % to about 90 wt. %, or from about 5 wt. % to about 70 wt. %, or from about 5 wt. % to about 50 wt. % of water.

The Inorganic Particulate Material

Surprisingly, it has been found that inorganic particulate materials in accordance with the first aspect of the invention enhances the formation of foam in a composition comprising a base and foaming agent by increasing foam volume and/or by reducing the average bubble size of the foam, upon and/or during topical application of the composition. In other words, the inorganic particulate material enhances the foam forming capability of the foaming agent. Further, the inclusion of inorganic particulate materials may enable a reduction in the amount of foaming agent, such as sodium laureth sulfate (also known as sodium laureth ether sulfate (SLES), which can be a skin or eye irritant, without loss of, or even increase, foam volume.

The inorganic particulate material has a $d_{50}$ of from about 0.1 μm to about 200 μm. In certain embodiments, when the inorganic particulate comprises or is perlite, the perlite has a $d_{50}$ of greater than about 10 μm, for example, equal to or greater than about 25 μm. In certain embodiments, the inorganic particulate material has a $d_{50}$ of from about 0.5 μm to about 150 μm, for example, from about 1 μm to about 125 μm, or from about 2 μm to about 125 μm, or from about 3 μm to about 125 μm, or from about 5 μm to about 125 μm, or from about 10 μm to about 125 μm, or from about 10 μm to about 100 μm, or from about 10 μm to about 90 μm, or from about 10 μm to about 80 μm, or from about 10 μm to about 70 μm, or from about 15 μm to about 70 μm, or from about 20 μm to about 60 μm, or from about 20 μm to about 50 μm, or from about 20 μm to about 45 μm, or from about 20 μm to about 40 μm. In certain embodiments, the inorganic particulate material has a $d_{50}$ of from about 0.1 μm to about 30 μm, for example, from about 0.5 μm to about 30 μm, or from about 1 μm to about 30 μm, or from about 2 μm to about 30 μm, or from about 1 μm to about 25 μm, or from about 1 μm to about 20 μm, or from about 1 μm or 2 μm to about 15 μm, or from about 1 μm or 2 μm to about 10 μm, or from about 5 μm to about 15 μm.

In certain embodiments, the inorganic particulate material and, thus, the composition, is free of crystalline silica.

In certain embodiments, the inorganic particulate material has a $d_{90}$ of no greater than about 500 μm, for example, no greater than about 475 μm, or no greater than about 450 μm, or no greater than about 425 μm, or no greater than about 400 μm, or no greater than about 375 μm, or no greater than about 350 μm, or no greater than about 325 μm, or no greater than about 300 μm, or no greater than about 275 μm, or no greater than about 250 μm, or no greater than about 225 μm, or no greater than about 200 μm, or no greater than about 175 μm, or no greater than about 150 μm, or no greater than about 125 μm, or no greater than about 100 μm. In certain embodiments, the inorganic particulate material has a $d_{90}$ of no greater than about 90 μm, for example, no greater than about 80 μm, or no greater than about 70 μm, or no greater than about 60 μm, or no greater than about 50 μm. In certain embodiments, the inorganic particulate material has a $d_{90}$ of from about 10 μm to about 100 μm, for example, or from about 15 μm to about 100 μm, or from about 20 μm to about 100 µm, or from about 25 µm to about 100 µm, or from about 30 µm to about 100 µm or from about 35 µm to about 100 µm.

In certain embodiments, the inorganic particulate material has a $d_{50}$ of from about 0.1 µm to about 70 µm and a $d_{90}$ of from about 10 µm to about 100 µm, for example, a $d_{50}$ from about 2 µm to about 70 µm and a $d_{90}$ of from about 10 µm to about 100 µm.

In certain embodiments, the inorganic particulate material is selected from the group consisting of perlite, an alkaline earth metal carbonate or sulphate, such as calcium carbonate, for example, natural calcium carbonate and/or precipitated calcium carbonate, magnesium carbonate, dolomite, gypsum, aluminosilicate (e.g. a hydrous kandite clay such as kaolin, halloysite or ball clay, an anhydrous (calcined) kandite clay such as metakaolin or fully calcined kaolin), talc, mica, diatomaceous earth, vermiculite, pumice, magnesium hydroxide, aluminium trihydrate, and combinations thereof.

In certain embodiments, the inorganic particulate material comprises or is perlite. The perlite may be substantially spherical perlite. By "substantially spherical" it is meant that individual particles of the inorganic particulate material have a generally (but not necessarily geometrically regular) spherical, spheroidal and/or ovoidal morphology, i.e., generally non-angular, as viewed using an optical microscope (e.g., a Keyence VHX-1000). For example, a substantially spherical particle may have a roundness of 1.15 or less, or 1.10 or less, or 1.05 or less. A suitable test method for measuring roundness is carried out by taking images of the particulates using an optical microscope, (e.g., a Keyence VHX-1000) on a contrasting background. The image is then transferred and opened using Leica image analysis software by Leica, Solms, Germany. The particles in the image are then drawn round and the roundness is calculated by the software.

In certain embodiments, the perlite is expanded perlite. Typically, expanded perlite includes one or more cells, or parts of cells, in which a cell is a void space partially or entirely surrounded by walls of glass, usually formed from expansion of gases when the glass is in the softened state. Processes for expanding perlite are well known in the art, and include heating perlite in air to a temperature of least about 700° C., typically between 800° C. and 1100° C., in an expansion furnace. Exemplary processes for producing expanded perlite are described in US-A-20060075930, the entire contents of which is hereby incorporated by reference. Expanded perlite typically has a bulk volume up to 20 times that of the unexpanded material. In certain embodiments, the substantially spherical perlite is expanded perlite. In certain embodiments, the perlite is expanded milled perlite.

In certain embodiments, the perlite is in the form of microspheres, which may be substantially closed and hollow. For present purposes, microspheres are defined as spherical particles in the micron size range. They can be hollow or solid. In certain embodiments, the cells are substantially hollow, i.e., substantially closed cell structures (e.g., sealed cavities normally filled with air). In certain embodiments, at least 50 wt. % of the perlite is in the form of microspheres, for example, at least about 60 wt. %, or at least about 70 wt. %, or at least about 80 wt. %, or at least about 90 wt. %, or at least about 95 wt. %, or at least about 99 wt. %, or substantially 100 wt. % of the perlite is in the form of microspheres. Perlite in the form of microspheres can be formed in accordance with the methods described in WO-A-2013053635, the entire contents of which is hereby incorporated by reference. Generally, in this process, perlite ore and propellant is fed into an upright furnace and falls along a drop section through multiple heating zones in a furnace shaft of the furnace. The perlite ore is heated to a critical temperature at which the surfaces of the perlite plasticize and perlite grains are expanded on the basis of the propellant.

In certain embodiments, the perlite, be it spherical, expanded, expanded spherical or expanded microspherical, is not milled, i.e., the perlite is not an expanded milled perlite.

In certain embodiments, the perlite, be it spherical, expanded spherical or expanded microspherical, is milled, i.e., the perlite is an expanded milled perlite. In certain embodiments, the perlite is not expanded microspherical perlite.

In certain embodiments, the perlite has a $d_{50}$ of greater than about 10 µm to up to about 100 µm, or greater than about 10 µm to up to about 90 µm, or greater than about 10 µm to up to about 80 µm, or greater than about 10 µm to up to about 70 µm, or from about 15 µm to about 70 µm, or from about 20 µm to about 60 µm, or from about 20 µm to about 50 µm, or from about 20 µm to about 45 µm, or from about 20 µm to about 40 µm.

In certain embodiments, the perlite has a $d_{50}$ of from about 3 µm to about 70 µm, for example, from about 3 µm to about 65 µm, or from about 3 µm to about 60 µm, or from about 3 µm to about 55 µm, or from about 3 µm to about 50 µm, or from about 3 µm to about 45 µm, or from about 3 µm to about 40 µm, or from about 3 µm to about 35 µm or from about 3 µm to about 30 µm, or from about 5 µm to about 30 µm.

In certain embodiments, the perlite has a $d_{50}$ of from about 3 µm to about 30 µm.

In certain embodiments, the inorganic particulate material is selected from one or more of perlite, diatomaceous earth, kaolin and talc, for example, selected from one or more of perlite, diatomaceous earth and talc.

In certain embodiments, the inorganic particulate comprises or is diatomaceous earth. In certain embodiments, the diatomaceous earth has a $d_{50}$ of from about 1 µm to about 30 µm, for example, from about 1 µm to about 25 µm, or from about 1 µm to about 20 µm, or from about 1 µm or 2 µm to about 15 µm, or from about 1 µm or 2 µm to about 10 µm, 1 µm or 2 µm to about 5 µm, or from about 5 µm to about 25 µm, or from about 10 µm to about 25 µm, or from about 15 µm to about 20 µm, or from about 15 µm to about 20 µm, or from about 10 µm to about 20 µm, or from about 10 µm to about 15 µm.

In certain embodiments, the diatomaceous earth has a $d_{50}$ of from about 2 µm to about 16 µm.

In certain embodiments in which the inorganic particulate material comprises or is diatomaceous earth, the composition comprises colouring(s). The colouring(s) may be incorporated in the base (e.g., cosmetically acceptable base) of the composition.

In certain embodiments, the inorganic particulate comprises or is talc. In certain embodiments, the talc has a $d_{90}$ of from about 5 µm to about 25 µm, or from about 5 µm to about 20 µm, or from about 10 µm to about 20 µm, or from about 10 µm to about 15 µm.

In certain embodiments, the inorganic particulate material comprises or is vermiculite. In certain embodiments, the vermiculite has a $d_{50}$ of from about 10 µm to about 100 µm, or from about 10 µm to about 90 µm, or greater than about 10 µm to about 80 µm, or greater than about 10 µm to about 70 µm, or from about 20 µm to about 70 µm, or from about 20 μm to about 60 μm, or from about 30 μm to about 60 μm, or from about 35 μm to about 55 μm, or from about 40 μm to about 50 μm.

In certain embodiments, the inorganic particulate material comprises or is kaolin. In certain embodiments, the kaolin has a $d_{50}$ of from about 0.1 to about 10 μm, for example, from about 0.1 μm to about 5 μm, or from about 0.1 μm to about 2 μm, or from about 0.1 μm to about 1 μm, or from about 0.2 to about 0.8 μm, or from about 0.3 to about 0.6 μm.

Unless otherwise specified, the particle size properties referred to herein for the inorganic particulate materials are as measured by the well known conventional method employed in the art of laser light scattering, using a CILAS 1064L particle size analyser, as supplied by CILAS (or by other methods which give essentially the same result). In the laser light scattering technique, the size of particles in powders, suspensions and emulsions may be measured using the diffraction of a laser beam, based on an application of Fraunhofer and Mie theory. Such a machine provides measurements and a plot of the cumulative percentage by volume of particles having a size, referred to in the art as the 'equivalent spherical diameter' (e.s.d), less than given e.s.d values. The mean particle size $d_{50}$ is the value determined in this way of the particle e.s.d at which there are 50% by volume of the particles which have an equivalent spherical diameter less than that $d_{50}$ value. The $d_{10}$ value is the value at which 10% by volume of the particles have an e.s.d less than that $d_{10}$ value. The $d_{90}$ value is the value at which 90% by weight of the particles have an e.s.d less than that $d_{90}$ value.

Any particular particle size distribution may be obtained using conventional methods known in the art, e.g., by screening. For example, screening may be carried out using an Alpine A-200 jet sieve, supplied by Hosakawa Alpine, Germany, with screens provided by Haver & Bocker. The screen apertures may be selected depending on the particle size distribution required. The inorganic particulate may be ground or milled prior to screening.

The Foaming Agent

The term "foaming agent" used herein refers to a material that facilitates the formation of foam upon and during topical application of the composition. As described herein, the inorganic particulate material therefore enhances the formation of foam by increasing foam volume and/or by reducing the average bubble size of the foam. In certain embodiments, topical application will be in the presence of an external source of water, e.g., from a tap or showerhead. In certain embodiments, the foaming agent comprises or is a surfactant or mixture of surfactants. Said surfactant or mixture of surfactants will have industry recognised foaming properties, i.e., they are known to facilitate the formation of foam. Such surfactants are known by those skilled in the art. It will also be understood that said surfactants will have cleansing properties, i.e., detergency properties, although their primary use may be as a foaming agent.

In certain embodiments, the foaming agent comprises or is one or more anionic surfactants, or one or more amphoteric surfactants, or one or more non-ionic surfactants, or any combination thereof.

Suitable anionic surfactants include, but are not limited to, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate, sodium lauryl sulfoacetate, sodium cocoyl isethionate, sodium methyl cocoyl taurate and mixtures thereof. The anionic surfactant may be, for example, an aliphatic sulfonate, such as a primary $C_8$-$C_{22}$ alkane sulfonate, primary $C_8$-$C_{22}$ alkane disulfonate, $C_8$-$C_{22}$ alkene sulfonate, $C_8$-$C_{22}$ hydroxyalkane sulfonate or alkyl glyceryl ether sulfonate.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, and mixtures thereof. The sulfobetaines may include stearyl dimethyl sulfopropyl betaine, lauryl dimethyl sulfoethyl betaine, lauryl bis-(2-hydroxyethyl) sulfopropyl betaine and mixtures thereof.

Suitable non-ionic surfactants include alcohols, acids, amides or alkyl phenols reacted with alkylene oxides, especially ethylene oxide either alone or with propylene oxide. Exemplary non-ionics are $C_6$-$C_{22}$ alkyl phenols-ethylene oxide condensates, the condensation products of $C_8$-$C_{18}$ aliphatic primary or secondary linear or branched alcohols with ethylene oxide, and products made by condensation of ethylene oxide with the reaction products of propylene oxide and ethylenediamine. Other non-ionics include long chain tertiary amine oxides. Other non-ionics are surfactants based on cocoamide and produced by reacting cocoamide with an alcohol amine, such as ethanolamine. Exemplary non-ionics include cocoamide MEA and cocoamide DEA. Other suitable non-ionics include alkyl polyglucosides such as decyl glucoside, lauryl glucoside and octyl glucoside.

In certain embodiments, the foaming agent comprises one or more of a lauryl sulfate, a laureth sulfate, an alkyl polyglucoside, a betaine, an alkyl glucoside, cocoamide MEA and cocoamide DEA. In such embodiments, the foaming agent may include an amount of sodium laureth sulfate In certain embodiments, the foaming agent comprises one or more of sodium laureth sulfate, sodium $C_{14-16}$ olefin sulfonate, sodium sodium lauryl sulfoacetate, sodium cocoyl isethionate, sodium methyl cocoyl taurate, cocoamidopropyl betaine, cocoamide MEA, and mixtures thereof. In such embodiments, the foaming agent may comprise sodium laureth sulfate.

In certain embodiments, the foaming agent comprises one or more anionic surfactants and one or more amphoteric surfactants, and optionally further comprises the non-ionic surfactant cocoamide MEA. In such embodiments, the one or more anionic surfactants may include sodium laureth sulfate.

In certain embodiments, the foaming agent comprises a mixture of at least two anionic surfactants and a betaine, such as cocamidopropyl betaine, and optionally further comprises cocoamide MEA.

The Base

In certain embodiments, the base is in the form a liquid, gel, emulsion, lotion or paste. In certain embodiments, the base is a liquid, lotion or gel. In certain embodiments, the base is a liquid. In certain embodiments, the base is a lotion. In certain embodiment, the base is a gel.

In certain embodiments, base comprises water, i.e., the base is aqueous. In certain embodiments, the base comprises at least about 30 wt. % water, based on the total weight of the base, for example, at least about 35 wt. % water, or at least about 40 wt. % water, or at least about 45 wt. % water, or at least about 50 wt. %, or at least about 55 wt. % water, or at least about 60 wt. % water, or at least about 65 wt. % water, or at least about 70 wt. % water, or at least about 75 wt. % water, or at least about 8 wt. % water, or at least about 85 wt. % water, or at least about 90 wt. % water. In certain embodiments, the base comprises from about 30 wt. % to about 90 wt. % water, based on the total weight of the base, for example, from about 35 wt. % to about 80 wt. % water, or from about 40 wt. % to about 75 wt. % water, or from about 45 wt. % to about 75 wt. % water, or from about 50 wt. % to about 75 wt. % water.

As described above, the base may comprise one or more of: thickening agent(s), suspending agent(s), skin conditioning/moisturising agent(s), hair conditioning agent(s) perfume(s), fragrance(s), opacifier(s), pearlescing agent(s), colouring(s), preservative(s), chelating agent(s); humectant(s), herb and/or plant extract(s), essential oil(s), protein(s), pH adjusting agent(s), and anti-microbial(s). These components may comprise up to about 20 wt. % of the composition, based on the total weight of the composition, for example, from about 0.1 wt. % to about 15 wt. %, or from about 1 wt. % to about 10 wt. %, or from about 0.5 wt. % to about 5 wt. % of the composition. The composition may further comprise surfactant(s) other than those of the foaming agent. Such surfactants are understood by those skilled in the art not to have any discernible foaming properties. These surfactants serve primarily as a cleansing agent, i.e., constituting or forming part of the detergent component of the composition. These surfactants may comprise up to about 30 wt. % of the composition, based on the total weight of the composition, for example, from about 1 wt. % to about 30 wt. % of the composition, or at least about 5 wt. %, or at least about 10 wt. %, or at least about 15 wt. %, or at least about 20 wt. %, or at least about 25 wt. % of the composition. The skilled person will be able to select suitable amounts of each component for incorporation in the base, based on the amount of the component in the final composition.

Suitable surfactants include cationic surfactants such as octenidine dihydrochloride, permanently charged quaternary ammonium surfactants such as alkyltrimethylammonium salts (e.g., cetyl trimethylammonium bromide, cetyl trimethylammonium chloride), cetylpyridinium chloride, benzalkonium chloride, benzethonium chloride, 5-Bromo-5-nitro-1,3-dioxane, dimethyldioctadecylammonium chloride, cetrimonium bromide and dioctadecyldimethylammonium bromide.

Suitable surfactants include any non-foaming anionic, amphoteric or non-inonic surfactants. Exemplary non-ionic surfactants include polyoxyethylene glycol sorbitan alkyl esters such as polysorbate, e.g., polysorbate 80.

The base may comprise one or more thickening agents or suspending agents (e.g., rheology modifier). Such agents may enhance the stability of the inorganic particulate material dispersed throughout the composition. Suitable thickening agents include water soluble/dispersable polymers, which may be cationic, anionic, amphoteric or non-ionic with molecular weights typically greater than about 100,000 Daltons. Such agents may also serve to increase the viscosity of the skin cleansing composition. Exemplary thickening or suspending agents include carbohydrate gums such as cellulose gum, microcrystalline cellulose, cellulose gel, hydroxyethyl cellulose, hydroxypropyl cellulose, sodium carboxymethylcellulose, methyl cellulose, ethyl cellulose, guar gum, gum karaya, gum tragacanth, gum arabic, gum acacia, gum agar, xanthan gum and mixtures thereof; modified and nonmodified starch granules and pregelatinized cold water soluble starch; emulsion polymers; cationic polymer such as modified polysaccharides; cationic modified cellulose; synthetic cationic polymer; cationic starches; cationic galactomannans; and high molecular weight polyethylene glycols, esters of ethylene glycol or esters of polyethylene glycol. Other suitable thickening/suspending agents include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters.

A thickening agent or suspending agent, such as a rheology modifier, when present, may be present in a total amount of from about 0.1 wt. % to about 50 wt. % by weight, based on the total weight of the composition, for example, from about 0.1 wt. % to about 35 wt. %, or from about 0.1 wt. % to about 20 wt. %, or from about 0.1 wt. % to about 10 wt. %, or from about 0.1 wt. % to about 5 wt. %. The skilled person will be able to select suitable amounts of each component for incorporation in the base, based on the amount of the component in the final composition.

A suitable amount of pH adjusting agent may be added, if necessary, to adjust the pH of the composition, particularly if the composition is a personal care composition. For example, a desirable pH range for shower or bath gels is typically from about 5.75 to 7. A desirable pH for shampoos is slightly wider from about 5 to 7. Most shampoos typically have a lower pH (around 5.5 to 6) than shower gels to match the hairs' natural acidity of around 4.5 to 5.5. Suitable pH adjusting agents in sodium hydroxide, sodium chloride and citric acid.

Suitable Amounts of Base, Foaming Agent and Inorganic Particulate Material

In certain embodiments, the total amount of inorganic particulate material present in the composition (e.g., personal care composition) is an amount of from about 0.1 wt. % to about 20 wt. %, based on the total weight of the composition, for example, from about 0.1 wt. % to about 15 wt. %, or from about 1.0 wt. % to about 15 wt. %, or from about 1.5 wt. % to about 12 wt. %, or from about 2.0 wt. % to about 10 wt. %, or from about 2.5 wt. % to about 10 wt. %, or from about 3.0 wt. % to about 9.0 wt. %, or from about 3.0 wt. % to about 8.5 wt. %, or from about 3.0 wt. % to about 8.0 wt. %, or from about 3.0 wt. % to about 7.5 wt. %, or from about 3.0 wt. % to about 7.0 wt. %, or from about 3.5 wt. % to about 7.0 wt. %, or from about 3.0 wt. % to about 6.5 wt. %, or from about 3.5 wt. % to about 6.0 wt. %, or from about 3.0 wt. % to about 6.0 wt. %, or from about 4.0 wt. % to about 7.5 wt. %, or from about 4.0 wt. % about 7.0 wt. %, or from about 4.0 wt. % to about 6.0 wt. %, or from about 4.0 wt. % to about 6.0 wt. %, or from about 4.5 wt. % to about 5.5 wt. %, or from about 4.5 wt. % to about 5.0 wt. %.

In certain embodiment, the total amount of inorganic particulate material present in the composition (e.g., personal care composition) is an amount of from about 3.5 wt.

% to about 6.5 wt. %. In such embodiments, the inorganic particulate may comprise, consist essentially of, or consist of perlite, for example, an expanded milled perlite. The perlite may have a $d_{50}$ of from greater than about 10 μm to about 70 μm, for example, from about 15 μm to about 40 μm, or from about 20 μm to about 30 μm, or a $d_{50}$ of equal to or greater than about 25 μm. The perlite may have a $d_{50}$ of from about 3 μm to about 70 μm, for example, a $d_{50}$ of from about 3 μm to about 65 μm, or from about 3 μm to about 60 μm, or from about 3 μm to about 55 μm, or from about 3 μm to about 50 μm or from about 3 μm to about 45 μm or from about 3 μm to about 40 μm or from about 3 μm to about 35 μm or from about 3 μm to about 30 μm, or from about 5 μm to about 30 μm.

In certain embodiments, the composition comprises at least about 50 wt. % base (e.g., cosmetically acceptable base), from about 1 wt. % to about 30 wt. % foaming agent, and from about 0.1 wt. % to about 20 wt. % inorganic particulate material, based on the total weight of the composition. In certain embodiments, the composition comprises at least about 55 wt. % base, for example, at least about 60 wt. %, or at least about 65 wt. %, or at least about 70 wt. %, or at least about 75 wt. %, or at least about 80 wt. % base. In certain embodiments, the composition comprises from about 50 wt. % to about 80 wt. % base, for example, from about 50 wt. % to about 75 wt. % base, or from about 50 wt. % to about 70 wt. % base, or from about 50 wt. % to about 65 wt. % base.

In certain embodiments, the composition comprises from about 2 wt. % to about 30 wt. % foaming agent, for example, from about 5 wt. % to about 25 wt. % foaming agent, for example, from about 10 wt. % to about 22.5 wt. % foaming agent, or from about 10 wt. to about 17.5 wt. % foaming agent, or from about 10 wt. % to about 15 wt. % foaming agent. In such embodiments, the foaming may comprise, consist essentially of, or consist of sodium laureth sulfate.

As described above, the incorporation of the inorganic particulate material as described herein enhances the formation of foam in a composition comprising a base and foaming agent by increasing foam volume and/or by reducing the average bubble size of the foam when the composition is diluted with water and shaken for a period to mimic the topical application of the composition in a wet environment, e.g., during showering or bathing. Thus, an inorganic particulate material having a $d_{50}$ of from about 0.1 μm to about 200 μm, may be used in a composition comprising a base and foaming agent (e.g., a personal care product such as a hair shampoo), for increasing the foam volume of the composition upon or during topical application of the composition. In certain embodiments, the inorganic particulate comprises or is perlite, and the perlite has a $d_{50}$ of greater than about 10 μm, for example, equal to or greater than about 25 μm. In certain embodiments, the inorganic particulate comprises or is perlite, and the perlite has a $d_{50}$ of from about 3 μm to about 70 μm, for example, from about 3 μm to about 30 μm. Likewise, an inorganic particulate material having a $d_{50}$ of from about 0.1 μm to about 200 μm, may be used in a composition comprising a base and foaming agent (e.g., a personal care product such as a hair shampoo), for reducing the average bubble size of the foam generated upon or during topical application of the composition. In certain embodiments, the inorganic particulate comprises or is perlite, and the perlite has a $d_{50}$ of greater than about 10 μm, for example, equal to or greater than about 25 μm. In certain embodiments, the inorganic particulate comprises or is perlite, and the perlite has a $d_{50}$ of from about 3 μm to about 70 μm, for example, from about 3 μm to about 30 μm.

Foam volume and average bubble size may be determined in accordance with the test methods described above and in the Examples below.

In certain embodiments, the foam volume of the composition comprising the inorganic particulate material is greater than the foam volume (in cm$^3$) of a comparable composition absent the inorganic particulate material, for example, the foam volume of the composition comprising the inorganic particulate material may be at least about 0.5% greater, or at least about 1.0% greater, or at least about 1.5% greater, or at least about 2.0% greater, or at least about 2.5% greater, or at least about 3.0% greater, or at least about 3.5% greater, or at least about 4.0% greater, or at least about 4.5% greater, or at least about 5.0% greater, or at least about 5.5% greater, or at least about 6.0% greater, or at least about 6.5% greater, or at least about 7.0% greater, or at least about 7.5% greater, or at least about 8.0% greater, or at least about 8.5% greater, or at least about 9.0% greater, or at least about 9.5% greater, or at least about 10.0% greater, or at least about 10.5% greater, or at least about 11.0% greater, or at least about 11.5% greater, or at least about 12.0% greater, or at least about 12.5% greater, or at least about 13.0% greater, or at least about 13.5% greater, or at least about 14.0% greater, or at least about 14.5% greater, or at least about 15.0% greater, or at least about 15.5% greater, or at least about 16.0% greater, or at least about 16.5% greater, or at least about 17.0% greater, or at least about 17.5% greater, or at least about 18.0% greater, or at least about 18.5% greater, or at least about 19.0% greater or at least about 19.5% greater, or at least about 20.0% greater than the foam volume (in cm$^3$) of a comparable composition absent the inorganic particulate material.

Additionally or alternatively, in certain embodiments, the composition comprising the inorganic particulate material has an average bubble size of the foam generated upon or during topical application of the composition which is smaller than the average bubble size of the foam generated upon or during topical application of a comparable composition absent the inorganic particulate material, for example, the average bubble size may be at least about 30% smaller, or at least about 40% smaller, or at least about 50% smaller, or at least about 60% smaller, or at least about 70% smaller, or at least about 75% smaller.

Without wishing to be bound by theory, it is postulated that the inorganic particulate material is providing nucleation sites for the bubbles, possibly related to the morphology of the particles in the particulate and particle size. With respect to perlite comprising air filled particles, the air in these particles may aid in bubble formation and stabilisation of the foam generated.

Further, smaller bubble size contributes to a creamier texture felt by the user. A creamier texture is generally desirable for the user. Thus, in certain embodiments, the composition comprising the inorganic particulate material has a creamier texture than a comparable composition absent the inorganic particulate material. In certain embodiments, therefore, the inorganic particulate material described herein is used in a composition comprising a base and a foaming agent (e.g., a personal care product such as a hair shampoo) to enhance the creaminess of the texture felt by the user.

Preparative Methods

Compositions in accordance with certain embodiments of the present invention may be made by conventional methods of preparing such compositions, e.g., hair shampoos, shower gels, etc. Generally, the inorganic particulate material is incorporated in the composition by combining the base, foaming agent(s) and inorganic particulate material in suitable amounts. The step of combining may include mixing, for example, shear mixing. Before, during or after incorporation of the inorganic particulate material, any additional components may be added to the composition. Typically, the majority of the components of the base and foaming agent will normally be prepared first, followed by combining with the inorganic particulate material and any other additional components. In certain embodiments, the mixing is carried out for a period of time sufficient to produce a homogeneous mixture.

For the avoidance of doubt, the present application is directed to the subject-matter described in the following numbered paragraphs:

1. A composition comprising a base, a foaming agent and inorganic particulate material having a $d_{50}$ of from about 0.1 μm to about 200 μm.

2. A composition according to numbered paragraph 1, wherein the composition is a personal care composition and the base is a cosmetically acceptable base.

3. A personal care composition according to numbered paragraph 2, wherein the personal care composition is a hair and/or skin cleansing composition.

4. A hair cleansing composition according to numbered paragraph 3, wherein the hair cleansing composition is a hair shampoo and/or conditioner.

5. A personal care composition according to numbered paragraph 2, wherein the personal care composition is a shaving foam or gel.

6. A composition according to numbered paragraph 1, wherein the composition is a dishwashing preparation.

7. A dishwashing preparation according to numbered paragraph 6, wherein the dishwashing preparation is a liquid or gel, for example, a washing-up liquid.

8. A composition according to any preceding numbered paragraph, wherein the inorganic particulate material has a $d_{50}$ of from about 3 μm to about 100 μm, for example, a $d_{50}$ of greater than about 10 μm to up to about 100 μm, for example, a $d_{50}$ of greater than about 10 μm to up to about 70 μm.

9. A composition according to any preceding numbered paragraph, wherein the foaming agent is a surfactant or mixture of surfactants.

10. A composition according to numbered paragraph 9, wherein the foaming agent comprises one or more anionic surfactants, or one or more amphoteric surfactants, or one or more non-ionic surfactants, or any combination thereof.

11. A composition according to numbered paragraph 9, wherein the inorganic particulate material is selected from the group consisting of perlite, an alkaline earth metal carbonate or sulphate, such as calcium carbonate, for example, natural calcium carbonate and/or precipitated calcium carbonate, magnesium carbonate, dolomite, gypsum, aluminosilicate (e.g., a hydrous kandite clay such as kaolin, halloysite or ball clay, an anhydrous (calcined) kandite clay such as metakaolin or fully calcined kaolin), talc, mica, diatomaceous earth, vermiculite, pumice, magnesium hydroxide, aluminium trihydrate, and combinations thereof.

12. A composition according to numbered paragraph 11, wherein the inorganic particulate material is perlite, diatomaceous earth, or talc, for example, expanded perlite, and may be milled or unmilled.

13. A composition according to numbered paragraph 12, wherein the expanded perlite is expanded milled perlite, optionally having a $d_{50}$ of from about 3 μm to about 70 μm.

14. A composition according to any preceding numbered paragraph, wherein the composition comprises from about 0.1 wt. % to about 10 wt. % of the inorganic particulate material, for example, from about 3 wt. % to about 7 wt. % of the inorganic particulate material, based on the total weight of the composition.

15. A composition according to any preceding numbered paragraph, wherein the composition comprises at least about 60 wt. % base and from about 1 wt. % to about 30 wt. % foaming agent, based on the total weight of the composition.

16. A composition according to any preceding numbered paragraph, wherein the base comprises at least about 50 wt. % water, and optionally further comprises one or more of: surfactant(s) other than those of the foaming agent, thickening agent(s), suspending agent(s), skin conditioning/moisturising agent(s), hair conditioning agent(s) perfume(s), fragrance(s), opacifier(s), pearlescing agent(s), colouring(s), preservative(s), chelating agent(s), humectants(s), herb and/or plant extract(s), essential oil(s), protein(s), pH adjusting agent(s), and anti-microbial(s).

17. A composition according to any preceding numbered paragraph, wherein the foam volume of the composition is greater than the foam volume of a comparable composition absent the inorganic particulate material.

18. A composition according to any preceding numbered paragraph, wherein the average bubble size of the foam generated upon or during topical application of the composition is smaller than the average bubble size of the foam generated upon or during topical application of a comparable composition absent the inorganic particulate material.

19. A diluted composition which is prepared by diluting a composition according to any preceding numbered paragraph with from about 1 wt. % to about 99 wt. % of water.

20. Use of an inorganic particulate material having a $d_{50}$ of from about 0.1 μm to about 200 μm, in a composition comprising a base and foaming agent, for increasing the foam volume of the composition upon or during topical application of the composition.

21. Use of an inorganic particulate material having a $d_{50}$ of from about 0.1 μm to about 200 μm, in a composition comprising a base and foaming agent, for reducing the average bubble size of the foam generated upon or during topical application of the composition.

22. A method for making a composition according to anyone of numbered paragraphs 1-18, said method comprising combining a base, foaming agent and inorganic particulate material as defined in any one of numbered paragraph 1-18 in suitable amounts.

EXAMPLES

Examples 1 and 2 relate to the first general aspect.
Example 3 relates to the second general aspect.
Examples 4 and 5 relate to the third general aspect.

Example 1

Test Methods
Scrub Feel

To assess the scrub feel, a panel of 12 subjects (6 male-6 female) is asked to use each gel in turn, scrubbing hands and arms, and give it a ranking on how good the gel feels. All of the gels prepared were tested against a standard gel comprising Gotalene® 135 colourless 26 micro-beads. The gel base for each gel is identical. The ranking is from 1 to 5, with 5 being very good feel. The test is run blind so that each subject does not know which inorganic particulate product (or Gotalene) they were using. The data was collected and an average rank calculated for each gel tested.

Abrasiveness

The abrasiveness of the inorganic particulate materials was compared to the Gotalene micro-beads and a shop bought exfoliating gel, Simple® exfoliating gel containing natural Luffa extract as the scrub particles.

Equipment:
- wet abrasion scrub machine (comprising a dual holder) supplied by Erichsen, Germany
- 100 μm high gloss black polyester film supplied by HiFi Industrial Film, Ltd, UK
- synthetic sponges, supplied by Sheen Instruments, UK
- Tri-Glossmaster, supplied by Sheen Instruments, UK
- Mettler AE 160 Analytical balance supplied by Mettler Toledo The test is based on BS7719:1194, Annex C (method for determination of scrub resistance). The sponges were soaked in warm water and weighed on an analytical balance to 8 g±0.5 g. The exfolient gel was then added to a sponge at 5 g±0.5 g. The sponges were placed into the holder on the scrub machine and point in contact with the polyester film. The scrub machine was set at 20 cycles (approximately 30 second duration) to simulate back and forth motion of scrubbing. Following completion of 20 cycles, the film was taken off, the residue washed off with warm water and left to dry. Once dry, the film panel was tested for gloss at 20° using the Tri-Glossmaster.

20° was selected as this angle is more sensitive to changes in gloss levels when analysing high gloss substrates. The gloss was measured and the percentage gloss retained calculated.

The test was repeated for the gel comprising the inorganic particulate materials and the Gotalene micro-beads.

Optical Images

Low magnification optical images of some of the inorganic particulate materials were taken (up to 200× magnification) using a Keyence VHX-1000 microscope, supplied by Keyence, UK.

Figure 3:
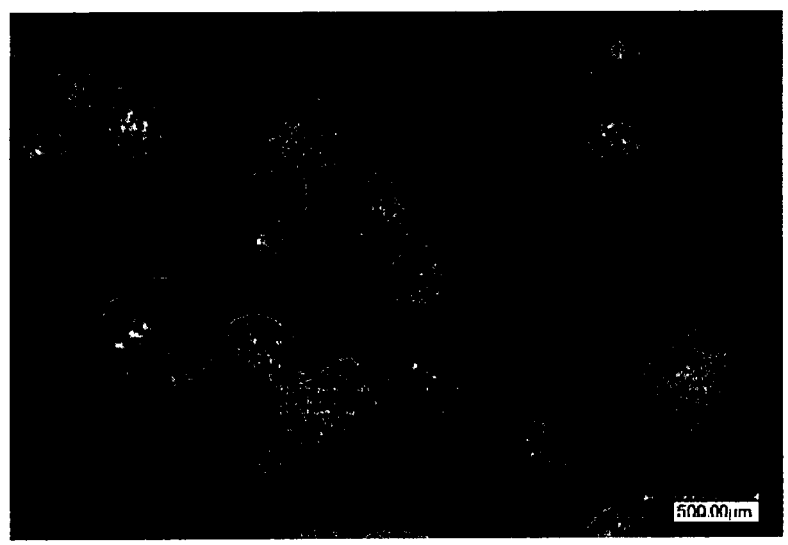
FIG. 3 is an optical image of a microspherical alumina, designated MA No. 2 in the Examples.
Figure 4:
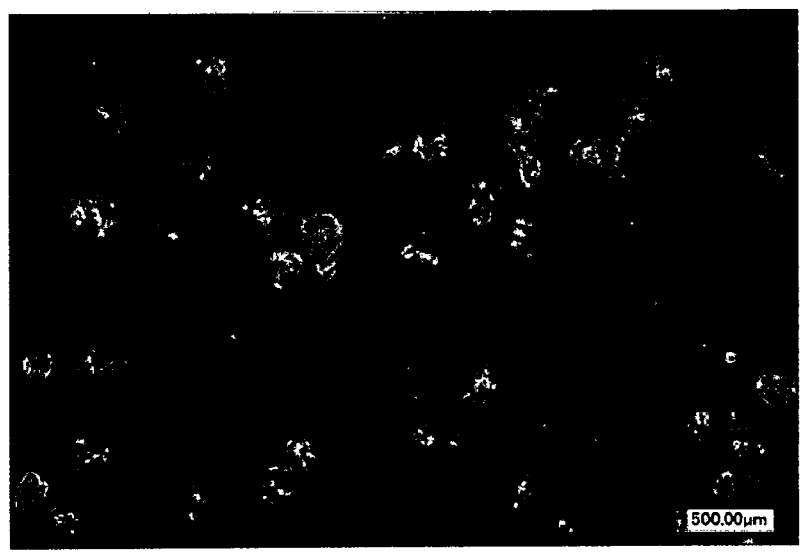
FIG. 4 is an optical image of a microspherical perlite, designated as PM No. 1. in the Examples.

FIG. 3 is an optical image of a microspherical alumina, MA No. 2. FIG. 4 is an optical image of a microspherical perlite, PM No. 1.

A series of inorganic particulate materials were added to gels in an amount of equivalent volume of 1.5 wt. % of Gotalene PE beads. The gel was a shop bought gel, Imperial Leather® Ocean Fresh revitalizing shower gel by PZ Cussons. The specific gravity of the gel was 1.016 g/cc. The gel showed a pseudoplastic behaviour to shear with a viscosity of about 20 Pa·s at low shear to about 2 Pa·s at high shear. A comparable gel comprising Gotalene® 135 colourless 26 microbeads was made. The gels were tested for scrub feel and abrasiveness.

Figure 2:
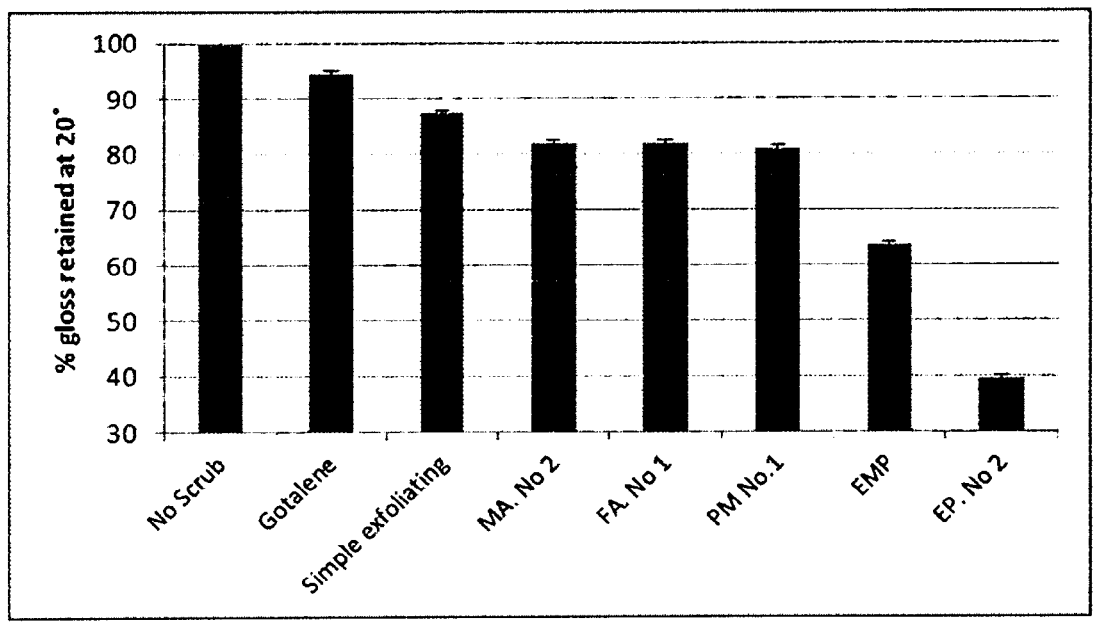
FIG. 2 is a graph summarising the abrasiveness of a number of inorganic particulate materials and comparative materials, as detailed in the Examples.

Details of each inorganic particulate material and composition tested and results are summarised in Table 1 and FIGS. 1 and 2.

TABLE 1

| Mineral/ microbead | Particle size (μm) | | | Density (g/cc) | Scrub feel average | Abrasiveness (% of gloss at 20°) |
|---|---|---|---|---|---|---|
| | $d_{10}$ | $d_{50}$ | $d_{90}$ | | | |
| Gotalene | | 205 | | 0.92 | 2.7 | 94 |
| EP No. 1 | 30 | — | 225 | 0.56 | 3.1 | — |
| EP No. 2 | 30 | 113 | 246 | 0.36 | 3.1 | 39 |
| EMP | 91 | 198 | 328 | 1.46 | 2.7 | 63 |
| PM No. 1 | 85 | 267 | 410 | 0.31 | 3.3 | 81 |
| FA No. 1 | 130 | — | 460 | 3.93 | 1.6 | 82 |
| FA No. 2 | 60 | — | 150 | 3.96 | 1.6 | — |

TABLE 1-continued

| Mineral/ microbead | Particle size (μm) | | | Density (g/cc) | Scrub feel average | Abrasiveness (% of gloss at 20°) |
|---|---|---|---|---|---|---|
| | $d_{10}$ | $d_{50}$ | $d_{90}$ | | | |
| MA No. 1 | 145 | — | 170 | 3.6 | 2.8 | — |
| MA No. 2 | 143 | 356 | 392 | 3.15 | 2.3 | 82 |

EP = expanded perlite;
EMP = expanded milled perlite;
PM = perlite microspheres;
FA = fused alumina;
MA = alumina microspheres Example 2

A sample of microspherical perlite, referred to herein as Perlite A, was obtained having the particle size distribution shown in Table 2 below. The crush strength of Perlite A was determined according to the test method described below. Results are summarised in Table 2.

TABLE 2

| | Perlite A |
|---|---|
| $d_{10}$ (μm) | 94 |
| $d_{50}$ (μm) | 170 |
| $d_{90}$ (μm) | 280 |
| Crush strength 30% vol decrease (KPa) | 1100 |
| Apparent density (g/cc) | 0.5 |

Crush Strength Test Method

This test measures the pressure required to crush a bed of material, held within a steel die set, by 30% of its original volume.

60 cm³ of sample is measured and transferred into the cylindrical die. The die has an internal diameter of 50.65 and an internal height of 60.9 mm. The die is gently shaken on a flat surface for 10 seconds to 'pack' the material down in the die. A piston (having a diameter complimentary to the diameter of the die) is placed gently on top of the sample in the die.

The height of the piston protruding above the top of the die is measured with a digital micrometer and recorded, which enables the bed depth of the sample before compression to be calculated.

A tensometer is set up with a 10 kN load cell fitted with clamp holder but no clamp. The die set with sample and piston is then placed under the cross-head of the tensometer and the cross-head is driven down so it is close to the top of the piston position in a tensometer.

The pressure is monitored as the piston is gradually driven into the die. The measurement is monitored and data analysed using Qmat software. The pressure at 30% volume compression is then obtained.

Bulk Density Test Method

The bulk density of a substance is the value obtained when the mass of the substance is divided by its contained volume, after the substance has been subjected to conditions of free pouring.

The test may be carried out on powders and granular materials. The materials are usually tested without prior drying, providing the material pours freely. The condition of free pouring is defined by the height of fall and the contained volume. The grain size of the test material is limited by the diameter of the funnel stem (see apparatus below).

Apparatus (ISO9001 Compliant)
  funnel, internal diameter 11 cm, stem diameter 1 cm, length 12 cm
  containing vessel; internal diameter 2.5 cm, depth 10 cm
  balance; capable of weighing 1000 g to 0.01 g
  retort stand, clamp and boss
  straight edge
  ruler to measure 7 cm
Method
  attach funnel to the retort stand
  tare the weight of the containing vessel
  place the containing vessel under the funnel
  adjust the clamp and boss so that the stem of the funnel is vertical and its end 7 cm above the top of the containing vessel
  pour the test material into the funnel until the containing vessel overflows
  level the test material across the top of the containing vessel with the straight edge
  weigh and record the net weight of the test material
Expression of Results
  bulk density (BD) is expressed as g/cm$^3$ and is calculated as follows:

$$BD = W/V$$

where W is the net weight of the test material recorded, and V is the volume of the containing vessel Example 3

Abrasiveness Test Method
Equipment:
  wet abrasion scrub machine (comprising a dual holder) supplied by Erichsen, Germany
  100 μm high gloss black polyester film supplied by HiFi Industrial Film, Ltd, UK
  synthetic sponges, supplied by Sheen Instruments, UK
  Tri-Glossmaster, supplied by Sheen Instruments, UK
  Mettler AE 160 Analytical balance supplied by Mettler Toledo The test is based on BS7719:1194, Annex C (method for determination of scrub resistance). The sponges were soaked in warm water and weighed on an analytical balance to 8 g±0.5 g. The cleansing composition was then added to a sponge at 5 g±0.5 g. The sponges were placed into the holder on the scrub machine and point in contact with the polyester film. The scrub machine was set at 20 cycles (approximately 30 second duration) to simulate back and forth motion of scrubbing. Following completion of 20 cycles, the film was taken off, the residue washed off with warm water and left to dry. Once dry, the film panel was tested for gloss at 20° using the Tri-Glossmaster. 20° was selected as this angle is more sensitive to changes in gloss levels when analysing high gloss substrates. The gloss was measured and the percentage gloss retained calculated.

The minerals were added at 1% wt to Clean Line Professional GP mild concentrated detergent (made by Prime Source, Birmingham UK) and scrubbed on the abrasion tester for 20 cycles.

Details of each inorganic particulate material and composition tested and results are summarised in Table 3.

TABLE 3

| Mineral/ microbead | Particle size (μm) | | | Density (g/cc) | Abrasiveness (% of gloss at 20°) |
|---|---|---|---|---|---|
| | $d_{10}$ | $d_{50}$ | $d_{90}$ | | |
| PM No. 1 | 25 | 65 | 95 | 1.95 | 94 |
| PM No. 2 | 90 | 200 | 270 | 0.56 | 88 |
| PM No. 3 | 90 | 260 | 400 | 0.40 | 74 |
| EP | 30 | 110 | 245 | 0.36 | 9 |
| AM No. 1 | 145 | 250 | 370 | 3.3 | — |
| AM No. 2 | 145 | 255 | 390 | 3.15 | — |

EP = expanded perlite (non-spherical);
PM = perlite microspheres;
AM = alumina microsphere Example 4

A series of shampoos were prepared, each comprising a different inorganic particulate material (i.e., different type or particle size distribution). Details of the inorganic particulate materials are given in Table 4 below.

For each shampoo, the inorganic particulate material was added to a commercially available shampoo such that each shampoo comprises 5 wt. % of the inorganic particulate material.

Each shampoo/inorganic particulate blend was diluted to 10% with water and mixed at low shear until the inorganic particulate material was fully incorporated. The mixer used was a Speed Mixer™ DAC 150FVZ by Synergy Devices Ltd, UK. The mixer speed was 300 rpm and the duration of mixing was one minute.

A sample of each diluted shampoo was transferred to a 150 ml polystyrene bottle and shaken by hand for 15 seconds, and the foam height recorded at T0 (i.e., immediately after shaking is stopped) and T5 mins. The foam volumes in the table below are at T0 only.

To measure average bubble size, images were taken up to 30 seconds after the shaking process stopped and the average bubble size determined using image analysis software. The image analysis software by Leica was used to analyse the images. The image was opened using the software and scale was calibrated and a sample of about 100 to 120 bubbles were drawn around. From this, the average area was calculated by the software as well as average length and breadth of the sample. A volume could be calculated then for average bubble size assuming the bubbles were ellipsoid in shape. i.e., the same breadth all the way round.

Figure 5:
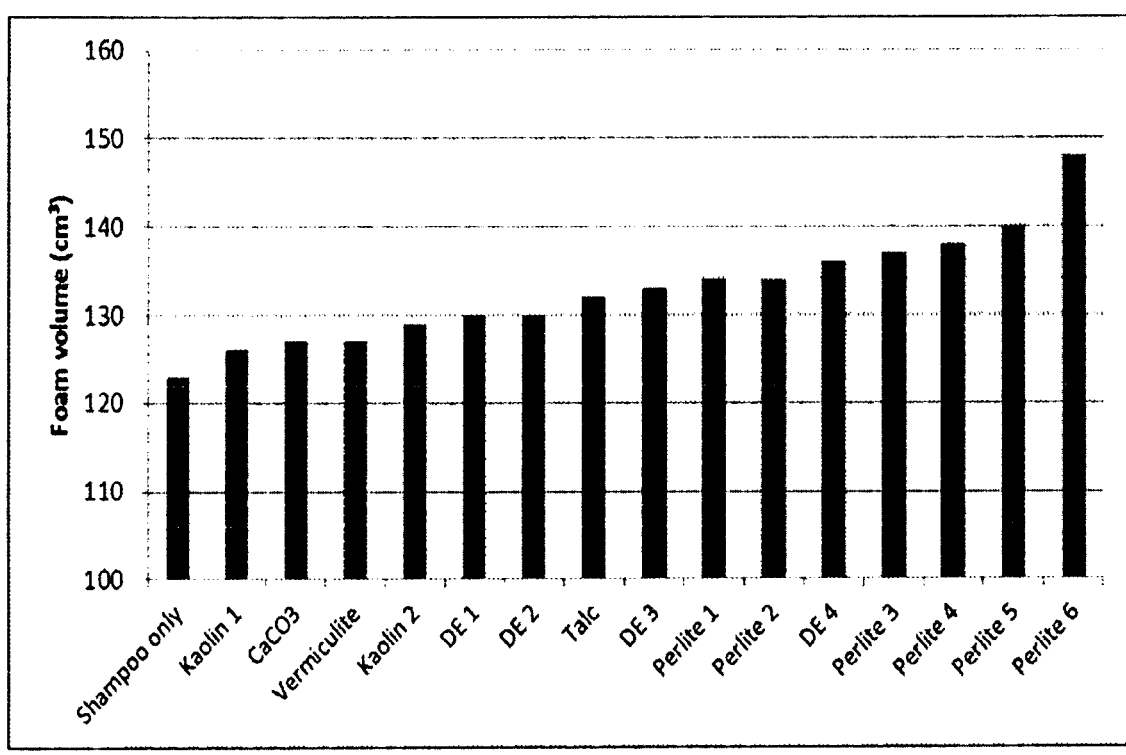
FIG. 5 is a graph summarising the foam volume of a comparative shampoo and a series of exemplary shampoos prepared in the Examples.

Results are summarized in Table 5 and FIG. 5.

Example 5

A series of shampoos were prepared, one comprising no inorganic particulate material, and four other shampoos each comprising 5 wt. % of an expanded milled perlite having a $d_{50}$ of 5 μm, and a different amount of sodium laureth sulfate (SLES) as a foaming agent. The difference in the amount of SLES was made up by water. Details of the inorganic particulate materials are given in Table 6 below. The shampoo without inorganic particulate material comprised 24 wt. % SLES. Foam volume for each shampoo was measured in accordance with the procedure described in Example 4.

TABLE 6

| 5% wt perlite addition | Foam volume (cm³) |
|---|---|
| Shampoo only | 66.8 |
| 10% w/w SLES reduction | 74.8 |
| 20% w/w SLES reduction | 73.2 |
| 30% w/w SLES reduction | 70.0 |
| 40% w/w SLES reduction | 60.4 |

TABLE 5

| 5% wt in shampoo | Average bubble area (mm²) | Average bubble size (mm³) | Foam volume (cm³) | % vol. increase | $d_{50}$ (μm) |
|---|---|---|---|---|---|
| Shampoo only | 5.1 | 3.42 | 123 | 0.0% | 0 |
| Kaolin 1 | 1.63 | 0.76 | 126 | 2.4% | 0.4 |
| CaCO3 | 1.76 | 1.15 | 127 | 3.3% | 6.5 |
| Vermiculite | 2 | 1.03 | 127 | 3.3% | 46 |
| Kaolin 2 | 1.4 | 0.69 | 129 | 4.9% | 0.2 |
| DE 1 | 1.98 | 1.18 | 130 | 5.7% | 12 |
| DE 2 | 2.5 | 1.74 | 130 | 5.7% | 18 |
| Talc | 2.57 | 1.43 | 132 | 7.3% | 12 |
| DE 3 | 1.4 | 0.82 | 133 | 8.1% | 5 |
| Perlite 1 | 2.14 | 1.17 | 134 | 8.9% | 40 |
| Perlite 2 | 1.85 | 1.15 | 134 | 8.9% | 30 |
| DE 4 | 1.1 | 0.53 | 136 | 10.6% | 3 |
| Perlite 3 | 2.4 | 1.57 | 137 | 11.4% | 65 |
| Perlite 4 | 1.1 | 0.48 | 138 | 12.2% | 25 |
| Perlite 5 | 1.03 | 0.44 | 140 | 13.8% | 20 |
| Perlite 6 | 0.68 | 0.12 | 148 | 20.3% | 5 |

The invention claimed is:

1. A personal care cleansing composition comprising:
    a cosmetically acceptable base selected from the group consisting of a liquid, a gel, an emulsion, a lotion or a paste; and
    an expanded inorganic particulate material having a density ranging from about 0.10 g/cc to about 2.0 g/cc, wherein the expanded inorganic particulate material comprises expanded spherical perlite, and at least 50 wt. % of the spherical perlite is in the form of microspheres that are substantially closed and hollow.

2. The personal care cleansing composition according to claim 1, wherein the expanded inorganic particulate material has a density ranging from about 0.10 g/cc to about 1.0 g/cc.

3. The personal care cleansing composition according claim 1, wherein the expanded inorganic particulate material has a density of from about 0.20 to about 0.50 g/cc.

4. The personal care cleansing composition according to claim 1, wherein the inorganic particulate has a d90 of no greater than about 500 μm.

5. The personal care cleansing composition according to claim 1, wherein the inorganic particulate material has a d10 of at least about 30 μm and a d90 of no greater than about 500 μm.

6. The personal care cleansing composition according to claim 1, wherein the inorganic particulate comprises microspheres of expanded spherical perlite and having a d10 of at least about 50 μm and a d90 of no greater than about 450 μm, and having a density of from about 0.20 to about 0.50 g/cc.

7. The personal care cleansing composition according to claim 1, wherein the inorganic particulate material has a d10 of at least about 10 μm and a d90 of no greater than about 450 μm.

8. The personal care cleansing composition according to claim 1, wherein the inorganic particulate is present in an amount of from about 0.1 wt. % to about 20 wt. %, based on the total weight of the personal care cleansing composition.

9. The personal care cleansing composition according to claim 1, wherein the inorganic particulate is present in an amount of from about 0.5 wt. % to about 5 wt. %.

10. The personal care cleansing composition according to claim 1, further comprising one or more of: surfactant(s), thickening agent(s), suspending agent(s), skin conditioning/moisturising agent(s), hair conditioning/moisturising agent(s), perfume(s), fragrance(s), opacifier(s), pearlescing agent(s), colouring(s), preservative(s), chelating agent(s), humectants(s), herb and/or plant extract(s), essential oil(s), protein(s), pH adjusting agent(s), and anti-microbial(s).

11. The personal care cleansing composition according to claim 1, wherein the personal care cleansing composition is a skin cleansing composition.

12. The personal care cleansing composition according to claim 11, wherein the skin cleansing composition is a soap.

13. The personal care cleansing composition according to claim 12, wherein the soap is a liquid soap.

14. The personal care cleansing composition according to claim 13, wherein the soap is selected from a hand soap, a face soap, a bodywash, a shower gel, a bath gel, a shaving foam, and a shaving gel.

15. The personal care cleansing composition according claim 1, wherein the personal care composition is a hair shampoo.

16. The personal care cleansing composition according claim 1, wherein the inorganic particulate material aids or provides exfoliation of the skin.

\* \* \* \* \*